(12) United States Patent
Payne et al.

(10) Patent No.: US 12,215,154 B2
(45) Date of Patent: Feb. 4, 2025

(54) COMPOSITIONS AND METHODS FOR TARGETING γδ T CELLS WITH CHIMERIC ANTIGEN RECEPTORS

(71) Applicant: THE TRUSTEES OF THE UNIVERSITY OF PENNSYLVANIA, Philadelphia, PA (US)

(72) Inventors: Aimee S. Payne, Merion Station, PA (US); Christoph T. Ellebrecht, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 1237 days.

(21) Appl. No.: 16/963,047

(22) PCT Filed: Jan. 18, 2019

(86) PCT No.: PCT/US2019/014227
§ 371 (c)(1),
(2) Date: Jul. 17, 2020

(87) PCT Pub. No.: WO2019/143961
PCT Pub. Date: Jul. 25, 2019

(65) Prior Publication Data
US 2020/0339687 A1  Oct. 29, 2020

Related U.S. Application Data

(60) Provisional application No. 62/619,146, filed on Jan. 19, 2018.

(51) Int. Cl.
  C07K 16/28 (2006.01)
  A61K 39/00 (2006.01)
  A61P 35/00 (2006.01)
  C07K 14/705 (2006.01)
  C07K 14/725 (2006.01)

(52) U.S. Cl.
  CPC ...... *C07K 16/2809* (2013.01); *A61K 39/4611* (2023.05); *A61K 39/4631* (2023.05); *A61K 39/4632* (2023.05); *A61K 39/464412* (2023.05); *A61P 35/00* (2018.01); *C07K 14/7051* (2013.01); *C07K 14/70517* (2013.01); *C07K 14/70578* (2013.01); *A61K 2239/28* (2023.05); *A61K 2239/31* (2023.05); *A61K 2239/38* (2023.05); *C07K 2317/56* (2013.01); *C07K 2317/622* (2013.01); *C07K 2319/02* (2013.01); *C07K 2319/03* (2013.01)

(58) Field of Classification Search
  CPC ............ C07K 16/2809; C07K 14/7051; C07K 14/70517; C07K 14/70578; C07K 2317/56; C07K 2317/622; C07K 2319/02; C07K 2319/03; C07K 2319/33; A61K 35/17; A61K 2239/28; A61K 39/4611; A61K 2239/31; A61K 2239/38; A61K 39/4631; A61K 39/4632; A61K 39/464412; A61K 48/00; A61P 35/00
  See application file for complete search history.

(56) References Cited

U.S. PATENT DOCUMENTS

| | | |
|---|---|---|
| 2014/0234348 A1 | 8/2014 | Scholler et al. |
| 2016/0046700 A1* | 2/2016 | Foster .............. C07K 14/70578 424/134.1 |
| 2016/0175358 A1 | 6/2016 | Jakobovits et al. |
| 2017/0073430 A1 | 3/2017 | Boontanrart et al. |
| 2017/0290858 A1 | 10/2017 | Zhao et al. |
| 2017/0334967 A1 | 11/2017 | Siegel et al. |

FOREIGN PATENT DOCUMENTS

| | | | |
|---|---|---|---|
| WO | 1993/003151 A1 | 2/1993 | |
| WO | 2008/118324 A2 | 10/2008 | |
| WO | 2012/154201 A1 | 11/2012 | |
| WO | 2015/132598 A1 | 9/2015 | |
| WO | 2016/025880 A1 | 2/2016 | |
| WO | 2016/172606 A1 | 10/2016 | |
| WO | WO-2016185035 A1 * | 11/2016 | .............. A61P 35/00 |
| WO | 2017/112741 A1 | 6/2017 | |
| WO | 2017/181119 A2 | 10/2017 | |

OTHER PUBLICATIONS

Dutta et al. Apoptosis Induced via Gamma Delta T Cell Antigen Receptor "Blocking" Antibodies: A Cautionary Tale. Front. Immunol. (2017) 8:776. (Year: 2017).*
Foppoli et al. Gamma-delta t-cell lymphomas. Eur J Haematol. (2015) 94(3):206-18. (Year: 2015).*
Torikai, H. et al., "A foundation for universal T-cell based immunotherapy: T cells engineered to express a CD19- specific chimeric-antigen-receptor and eliminate expression of endogenous TCR", Blood, Jun. 14, 2012, 119 (24):5697-5705.
Wei, E. et al., "γδ T-Cell Acute Lymphoblastic Leukemia/Lymphoma: Discussion of Two Pediatric Cases and Its Distinction from Other Mature γδ T-Cell Malignancies", Case Rep Hematol; Sep. 24, 2017:5873015, 7 pages.
Matos, D.M. et al.,"Gammadelta and alphabeta T-cell acute lymphoblastic leukemia: comparison of their clinical and immunophenotypic features", Haematologica Feb. 2005; 90(2):264-6.

(Continued)

*Primary Examiner* — Brad Duffy
*Assistant Examiner* — Amber K Faust
(74) *Attorney, Agent, or Firm* — Saul Ewing LLP; Kathryn Doyle

(57) ABSTRACT

The invention includes compositions comprising a chimeric antigen receptor (CAR) specific for an GD T Cell receptor (anti-GD TCR CAR), vectors comprising the same, compositions comprising anti-GD TCR CAR vectors packaged in viral particles, and recombinant T cells or other effector cells comprising the anti-GD TCR CAR of the invention. The invention also includes methods of making a genetically modified T cell expressing an anti-GD TCR CAR wherein the expressed CAR comprises an extracellular domain that binds to GD T cells or to cells expressing a GD TCR.

22 Claims, 9 Drawing Sheets
Specification includes a Sequence Listing.

(56) References Cited

OTHER PUBLICATIONS

Rodriguez-Pinilla, S.M. et al., "TCR-γ expression in primary cutaneous T-cell lymphomas", Am J Surg Pathol Mar. 2013; 37(3):375-84.
Toro, J.R. et al., "Gamma-delta T-cell phenotype is associated with significantly decreased survival in cutaneous T-cell lymphoma", Blood, May 1, 2003;101:3407-3412.
Koenecke, C. et al., "In vivo application of mAb directed against the γδ TCR does not deplete but generates "invisible" γδ T cells", Eur. J. Immunol., Jan. 29, 2009, 39: 372-379.
Zhou, J. et al., "Anti-γδ TCR antibody-expanded γδ T cells: a better choice for the adoptive immunotherapy of lymphoid malignancies", Cellular & Molecular Immunology, 2012, vol. 9, pp. 34-44.
The Extended European Search Report dated Dec. 10, 2021 of counterpart European Application No. 197416985.5.
PCT/US2019/014227—International Search Report and Written Opinion dated Apr. 23, 2019.

\* cited by examiner

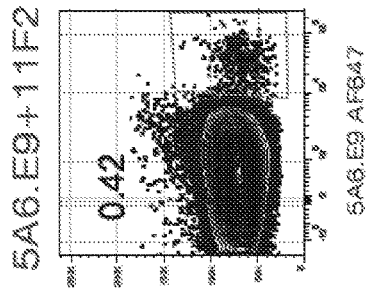
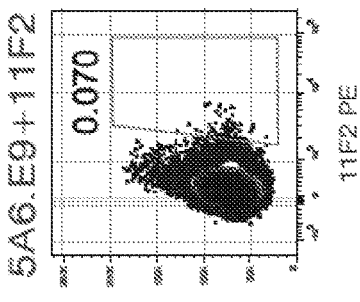
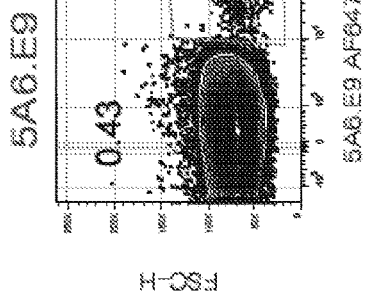
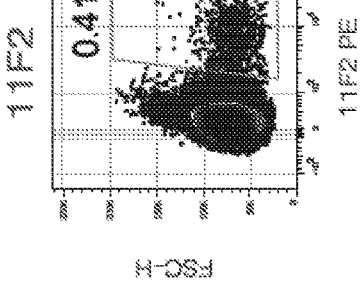
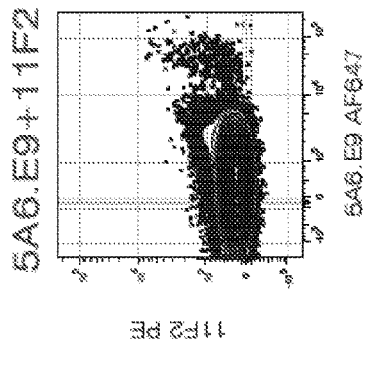
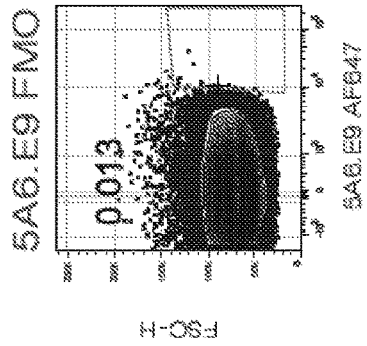
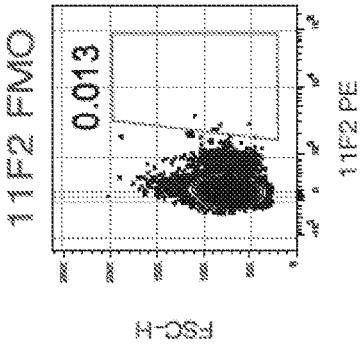
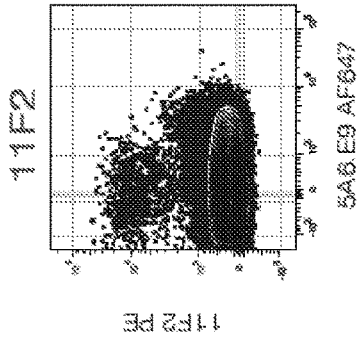
FIG. 9A  FIG. 9B  FIG. 9C

SEQUENCE LISTING

```
<160> NUMBER OF SEQ ID NOS: 17

<210> SEQ ID NO 1
<211> LENGTH: 486
<212> TYPE: PRT
<213> ORGANISM: artificial sequence
<220> FEATURE:
<223> OTHER INFORMATION: Synthetic Construct

<400> SEQUENCE: 1

Met Glu Phe Gly Leu Ser Trp Leu Phe Leu Val Ala Ile Leu Lys Gly
1               5                   10                  15

Val Gln Cys Gly Ser Asp Ile Gln Met Thr Gln Thr Thr Ser Ile Leu
            20                  25                  30

Ser Ala Ser Leu Gly Asp Arg Val Thr Ile Thr Cys Arg Ala Ser Gln
        35                  40                  45

Asp Ile Ser Asn Tyr Leu Asn Trp Tyr Gln Gln Asn Pro Asp Gly Thr
    50                  55                  60

Val Lys Leu Leu Ile Tyr Tyr Thr Ser Arg Leu His Ser Gly Val Pro
65                  70                  75                  80

Ser Arg Phe Ser Gly Ser Gly Ser Gly Thr Glu Tyr Ser Leu Thr Ile
                85                  90                  95

Lys Asn Leu Glu Gln Glu Asp Ile Ala Thr Tyr Phe Cys Gln Gln Gly
            100                 105                 110

Asn Met Val Pro Phe Thr Phe Gly Ser Gly Thr Lys Leu Glu Ile Lys
        115                 120                 125

Gly Gly Gly Gly Ser Gly Gly Gly Ser Gly Gly Gly Ser Gln
    130                 135                 140

Val Gln Leu Lys Glu Ser Gly Pro Gly Leu Val Ala Pro Ser Gln Ser
145                 150                 155                 160
```

```
Leu Ser Ile Thr Cys Thr Val Ser Gly Phe Ser Leu Thr Ser Tyr Gly
            165                 170                 175

Val His Trp Val Arg Gln Pro Pro Gly Lys Gly Leu Glu Trp Leu Gly
        180                 185                 190

Val Ile Trp Ala Ser Gly Thr Thr Asp Tyr Asn Ser Ala Leu Met Ser
    195                 200                 205

Arg Leu Thr Ile Ser Lys Asp Asn Ser Lys Ser Gln Val Phe Leu Arg
210                 215                 220

Met Asn Ser Leu Gln Thr Asp Asp Thr Ala Met Tyr Tyr Cys Ala Arg
225                 230                 235                 240

Glu Thr Thr Ala Ser Phe Gly Tyr Trp Gly Leu Gly Thr Leu Val Thr
                245                 250                 255

Val Ser Ala Ala Ser Thr Thr Thr Pro Ala Pro Arg Pro Pro Thr Pro
            260                 265                 270

Ala Pro Thr Ile Ala Ser Gln Pro Leu Ser Leu Arg Pro Glu Ala Cys
        275                 280                 285

Arg Pro Ala Ala Gly Gly Ala Val His Thr Arg Gly Leu Asp Phe Ala
    290                 295                 300

Cys Asp Ser Gly Ile Tyr Ile Trp Ala Pro Leu Ala Gly Thr Cys Gly
305                 310                 315                 320

Val Leu Leu Leu Ser Leu Val Ile Thr Leu Tyr Cys Lys Arg Gly Arg
                325                 330                 335

Lys Lys Leu Leu Tyr Ile Phe Lys Gln Pro Phe Met Arg Pro Val Gln
            340                 345                 350

Thr Thr Gln Glu Glu Asp Gly Cys Ser Cys Arg Phe Pro Glu Glu Glu
        355                 360                 365

Glu Gly Gly Cys Glu Leu Arg Val Lys Phe Ser Arg Ser Ala Asp Ala
    370                 375                 380

Pro Ala Tyr Gln Gln Gly Gln Asn Gln Leu Tyr Asn Glu Leu Asn Leu
385                 390                 395                 400

Gly Arg Arg Glu Glu Tyr Asp Val Leu Asp Lys Arg Arg Gly Arg Asp
                405                 410                 415

Pro Glu Met Gly Gly Lys Pro Arg Arg Lys Asn Pro Gln Glu Gly Leu
            420                 425                 430

Tyr Asn Glu Leu Gln Lys Asp Lys Met Ala Glu Ala Tyr Ser Glu Ile
        435                 440                 445

Gly Met Lys Gly Glu Arg Arg Arg Gly Lys Gly His Asp Gly Leu Tyr
    450                 455                 460

Gln Gly Leu Ser Thr Ala Thr Lys Asp Thr Tyr Asp Ala Leu His Met
465                 470                 475                 480

Gln Ala Leu Pro Pro Arg
                485

<210> SEQ ID NO 2
<211> LENGTH: 19
<212> TYPE: PRT
<213> ORGANISM: Homo sapiens

<400> SEQUENCE: 2

Met Glu Phe Gly Leu Ser Trp Leu Phe Leu Val Ala Ile Leu Lys Gly
1               5                   10                  15

Val Gln Cys

<210> SEQ ID NO 3
<211> LENGTH: 107
```

<212> TYPE: PRT
<213> ORGANISM: Mus musculus

<400> SEQUENCE: 3

Asp Ile Gln Met Thr Gln Thr Thr Ser Ile Leu Ser Ala Ser Leu Gly
1               5                   10                  15

Asp Arg Val Thr Ile Thr Cys Arg Ala Ser Gln Asp Ile Ser Asn Tyr
            20                  25                  30

Leu Asn Trp Tyr Gln Gln Asn Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Glu Tyr Ser Leu Thr Ile Lys Asn Leu Glu Gln
65                  70                  75                  80

Glu Asp Ile Ala Thr Tyr Phe Cys Gln Gln Gly Asn Met Val Pro Phe
                85                  90                  95

Thr Phe Gly Ser Gly Thr Lys Leu Glu Ile Lys
            100                 105

<210> SEQ ID NO 4
<211> LENGTH: 15
<212> TYPE: PRT
<213> ORGANISM: artificial sequence
<220> FEATURE:
<223> OTHER INFORMATION: Synthetic Construct

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 116
<212> TYPE: PRT
<213> ORGANISM: Mus musculus

<400> SEQUENCE: 5

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Gly Val His Trp Val Arg Gln Pro Pro Gly Lys Gly Leu Glu Trp Leu
        35                  40                  45

Gly Val Ile Trp Ala Ser Gly Thr Thr Asp Tyr Asn Ser Ala Leu Met
    50                  55                  60

Ser Arg Leu Thr Ile Ser Lys Asp Asn Ser Lys Ser Gln Val Phe Leu
65                  70                  75                  80

Arg Met Asn Ser Leu Gln Thr Asp Asp Thr Ala Met Tyr Tyr Cys Ala
                85                  90                  95

Arg Glu Thr Thr Ala Ser Phe Gly Tyr Trp Gly Leu Gly Thr Leu Val
            100                 105                 110

Thr Val Ser Ala
115

<210> SEQ ID NO 6
<211> LENGTH: 71
<212> TYPE: PRT
<213> ORGANISM: Homo sapiens

<400> SEQUENCE: 6

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp Ser Gly Ile
            35                  40                  45

Tyr Ile Trp Ala Pro Leu Ala Gly Thr Cys Gly Val Leu Leu Leu Ser
    50                  55                  60

Leu Val Ile Thr Leu Tyr Cys
65              70

<210> SEQ ID NO 7
<211> LENGTH: 42
<212> TYPE: PRT
<213> ORGANISM: Homo sapiens

<400> SEQUENCE: 7

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
                20                  25                  30

Pro Glu Glu Glu Glu Gly Gly Cys Glu Leu
            35                  40

<210> SEQ ID NO 8
<211> LENGTH: 112
<212> TYPE: PRT
<213> ORGANISM: Homo sapiens

<400> SEQUENCE: 8

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
                20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65              70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 9
<211> LENGTH: 1461
<212> TYPE: DNA
<213> ORGANISM: Artificial Sequence
<220> FEATURE:
<223> OTHER INFORMATION: Synthetic Construct

<400> SEQUENCE: 9
atggagtttg ggctgagctg gcttttttctt gtggctattt taaaaggtgt ccagtgcgga      60
tccgatatcc aaatgacgca aactacgtct atcctgtctg cctccttggg cgaccgggtg     120
acgattacgt gccgggcatc tcaagatatt agtaactatc ttaactggta tcaacagaac     180
cctgacggaa cggtgaaatt gctcatttac tacacttcta gacttcatag tggcgtgccg     240

-continued

```
tccagatttt ccggaagtgg gtcaggtaca gaatactcac tgactattaa gaacctggaa      300
caagaggaca tagccacata tttttgtcag caaggtaata tggtcccttt taccttcggc      360
agtggtacta agctcgaaat aaagggagga gggggtagcg gaggtggcgg ctcaggcggc      420
ggcggcagtc aggttcaact taaggaatcc ggtcccggtc ttgtagcgcc aagtcagtct      480
ctctctatca cttgtacggt atccgggttc tcccttacgt cctacggggt acactgggtt      540
cgacaaccac ccgaaagggg cctggagtgg ttgggcgtca tatgggcaag cggaactacg      600
gattataact ctgcccttat gtctcgcctc accatttcta aagataatag taaaagccag      660 gttttttcttc gcatgaactc tctccaaact gatgacacag caatgtacta ctgcgccagg      720
gagactacag cgagtttcgg ttattggggc ttgggcacac tggtcacagt ttcagcagct      780
agcaccacga cgccagcgcc gcgaccacca acaccggcgc ccaccatcgc gtcgcagccc      840
ctgtccctgc gcccagaggc gtgccggcca cggcggggg gcgcagtgca cacgaggggg      900
ctggacttcg cctgtgattc cggaatctac atctgggccc ctctggccgg cacctgtggc      960
gtgctgctgc tgtccctggt catcaccctg tactgcaagc ggggcagaaa gaagctgctg     1020
tacatcttca gcagcccctt catgcggcct gtgcagacca cacaggaaga ggacggctgt     1080
agctgtagat tccccgagga agaggaaggc ggctgcgagc tgagagtgaa gttcagcaga     1140
agcgccgacg cccctgccta tcagcagggc cagaaccagc tgtacaacga gctgaacctg     1200
ggcagacggg aggaatacga cgtgctggac aagagaagag gccggacccc tgagatgggc     1260
ggcaagccca gacggaagaa cccccaggaa ggcctgtata cgaactgca gaaagacaag     1320 atggccgagg cctacagcga gatcggcatg aagggcgagc ggagaagagg caagggccat     1380
gacggcctgt accagggcct gagcaccgcc accaaggaca cctacgacgc cctgcacatg     1440
caggccctgc ctccaagatg a                                                1461
```

\<210> SEQ ID NO 10
\<211> LENGTH: 57
\<212> TYPE: DNA
\<213> ORGANISM: Homo sapiens

\<400> SEQUENCE: 10

```
atggagtttg ggctgagctg cttttttctt gtggctattt taaaaggtgt ccagtgc           57
```

\<210> SEQ ID NO 11
\<211> LENGTH: 320
\<212> TYPE: DNA
\<213> ORGANISM: Artificial Sequence
\<220> FEATURE:
\<223> OTHER INFORMATION: Synthetic Construct

\<400> SEQUENCE: 11

```
gatatccaaa tgacgcaaac tacgtctatc ctgtctgcct ccttgggcga ccgggtgacg       60
attacgtgcc gggcatctca agatattagt aactatctta actggtatca acagaaccct      120
gacggaacgg tgaaattgct catttactac acttctagac ttcatagtgg cgtgccgtcc      180
agattttccg gaagtgggtc aggtacagaa tactcactga ctattaagaa cctggaacaa      240
gaggacatag ccacatattt ttgtcagcaa ggtaatatgg tccctttac cttcggcagt      300 ggtactaagc tcgaaataaa                                                   320
```

\<210> SEQ ID NO 12
\<211> LENGTH: 46
\<212> TYPE: DNA
\<213> ORGANISM: Artificial Sequence

```
<220> FEATURE:
<223> OTHER INFORMATION: Synthetic Construct

<400> SEQUENCE: 12 ggg aggaggg ggtagcggag gtggcggctc aggcggcggc ggcagt              46

<210> SEQ ID NO 13
<211> LENGTH: 348
<212> TYPE: DNA
<213> ORGANISM: Artificial Sequence
<220> FEATURE:
<223> OTHER INFORMATION: Synthetic Construct

<400> SEQUENCE: 13
caggttcaac ttaaggaatc cggtcccggt cttgtagcgc aagtcagtc tctctctatc    60 acttgtacgg tatccgggtt ctcccttacg tcctacgggg tacactgggt tcgacaacca  120
cccggaaagg gcctggagtg gttgggcgtc atatgggcaa gcggaactac ggattataac  180
tctgccctta tgtctcgcct caccatttct aaagataata gtaaaagcca ggttttctt   240 cgcatgaact ctctccaaac tgatgacaca gcaatgtact actgcgccag ggagactaca  300
gcgagtttcg gttattgggg cttgggcaca ctggtcacag tttcagca              348

<210> SEQ ID NO 14
<211> LENGTH: 213
<212> TYPE: DNA
<213> ORGANISM: Homo sapiens

<400> SEQUENCE: 14
accacgacgc cagcgccgcg accaccaaca ccggcgccca ccatcgcgtc gcagcccctg    60
tccctgcgcc cagaggcgtg ccggccagcg gcggggggcg cagtgcacac gaggggggctg 120 gacttcgcct gtgattccgg aatctacatc tgggcccctc tggccggcac ctgtggcgtg  180
ctgctgctgt ccctggtcat caccctgtac tgc                              213

<210> SEQ ID NO 15
<211> LENGTH: 126
<212> TYPE: DNA
<213> ORGANISM: Homo sapiens

<400> SEQUENCE: 15
aagcggggca gaaagaagct gctgtacatc ttcaagcagc ccttcatgcg gcctgtgcag    60
accacacagg aagaggacgg ctgtagctgt agattccccg aggaagagga aggcggctgc   120
gagctg                                                            126

<210> SEQ ID NO 16
<211> LENGTH: 336
<212> TYPE: DNA
<213> ORGANISM: Homo sapiens

<400> SEQUENCE: 16
agagtgaagt tcagcagaag cgccgacgcc cctgcctatc agcagggcca gaaccagctg    60
tacaacgagc tgaacctggg cagacgggag gaatacgacg tgctggacaa gagaagaggc   120
cgggaccctg agatgggcgg caagcccaga cggaagaacc cccaggaagg cctgtataac   180
gaactgcaga agacaagat ggccgaggcc tacagcgaga tcggcatgaa gggcgagcgg    240
agaagaggca aggccatga cggcctgtac cagggcctga gcaccgccac caaggacacc    300
tacgacgccc tgcacatgca ggccctgcct ccaaga                           336
```

```
<210> SEQ ID NO 17
<211> LENGTH: 69
<212> TYPE: PRT
<213> ORGANISM: Homo sapiens

<400> SEQUENCE: 17

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
            35                  40                  45

Trp Ala Pro Leu Ala Gly Thr Cys Gly Val Leu Leu Leu Ser Leu Val
    50                  55                  60

Ile Thr Leu Tyr Cys
65
```

US 12,215,154 B2

COMPOSITIONS AND METHODS FOR TARGETING γδ T CELLS WITH CHIMERIC ANTIGEN RECEPTORS

CROSS-REFERENCE TO RELATED APPLICATIONS

The present application is a 35 U.S.C. § 371 national phase application from, and claims priority to, International Application No. PCT/US2019/014227, filed Jan. 18, 2019, which claims priority under 35 U.S.C. § 119 (e) to U.S. Provisional Application No. 62/619,146, filed Jan. 19, 2018, all of which applications are incorporated herein by reference in their entireties.

STATEMENT REGARDING FEDERALLY SPONSORED RESEARCH OR DEVELOPMENT

This invention was made with government support under AR068288, awarded by the National Institutes of Health. The government has certain rights in the invention.

BACKGROUND OF THE INVENTION

Gamma delta T cell (γδ T cells, or GD T cells) represent a minor subset of cells within peripheral blood and lymphoid organs in humans (less than 10%). γδ T cells combine features of the adaptive and the innate immune response. While they develop in the thymus and undergo VDJ recombination resulting in a diverse T cell receptor repertoire, their reactivity is not MHC-restricted, they react to non-peptide antigens that are presented by stressed cells similar to pathogen-associated molecular patterns, and they predominantly display an effector phenotype that allows for rapid, innate-like activation.

Additionally, they display a characteristic tropism for specific tissues, namely liver, respiratory/digestive/reproductive mucosa and skin. As any immune cell type can undergo malignant transformation resulting in leukemia or lymphoma, γδ T cell lymphomas (GDTCLs) have been described in accordance with their tissue tropism, i.e. hepatosplenic GDTCL, mucosal GDTCL and cutaneous GDTCL. A common feature of GDTCLs is their poor prognosis. The median survival of cutaneous GDTCL is 15 months and the disease is highly resistant to known treatment modalities, similar to other malignancies with poor prognosis such as glioblastoma, pancreatic and ovarian cancer. The World Health Organization (WHO) recognized the unmet therapeutic need and the unique morphologic and outcome characteristics of cutaneous GDTCL by making it an independent entity in its latest lymphoma classification in 2016. In addition, γδ TCRs are expressed by approximately 5% of all cutaneous T cell lymphomas, and by 10% of T cell acute lymphoblastic leukemias (Wei et al., *Case Rep Hematol;* 2017:5873015; Matos et al., *Haematologica* 2005; 90(2):264-6; Gibson et al. *Clinical Case Reports* 2015; 3(1):34-38; Rodriguez-Pinilla et al. *Am J Surg Pathol* 2013; 37(3):375-84). γδ cells have also been implicated in a number of inflammatory and autoimmune diseases (e.g. polymyositis, Hohlfeld R. et al., *NEJM* 1991: 324, 877-881).

Recently, the use of gene-engineered T cells (i.e. adoptive immunotherapy) has been a major breakthrough in the treatment of hematopoietic malignancies. Using chimeric antigen receptors (CARs), T cells can be re-directed to specifically kill cancer cells if they express the antigen targeted by the CAR. This therapeutic strategy has a major advantage: CAR T cells show favorable kinetics compared to conventional drugs because they expand and persist in the patient's body. As a consequence, CAR T cells have, in some circumstances, induced lasting remission of late-stage leukemia, underscoring their ability to effect long-term, cross-compartment surveillance to prevent cancer recurrence.

A need exists for a therapy that targets γδ T cell lymphomas (GDTCLs). This invention addresses this need.

SUMMARY OF THE INVENTION

Provided is an isolated nucleic acid sequence encoding an anti-γδ T cell Receptor Chimeric Antigen Receptor (anti-GD TCR CAR), wherein the isolated nucleic acid sequence comprises a nucleic acid sequence encoding an extracellular domain comprising an anti-γδ T cell Receptor (anti-GD TCR) or fragment thereof, a nucleic acid sequence encoding a transmembrane domain, a nucleic acid sequence encoding an intracellular domain of a costimulatory molecule, and a nucleic acid sequence encoding a signaling domain. In some embodiments, the anti-GD TCR CAR comprises the amino acid sequence of SEQ ID NO: 1. In some embodiments, the nucleic acid sequence encoding the anti-GD TCR CAR comprises SEQ ID NO: 9. In some embodiments, the anti-GD TCR or fragment thereof is encoded by at least one nucleic acid sequence encoding a light chain comprising the amino acid sequence of SEQ ID NO: 3 or a heavy chain comprising the amino acid sequence of SEQ ID NO:5. In some embodiments, the anti-GD TCR or fragment thereof comprises at least a light chain encoded by a nucleic acid sequence of SEQ ID NO: 11 or a heavy chain encoded by a nucleic acid sequence of SEQ ID NO: 13.

In some embodiments, the isolated nucleic acid sequence encoding an anti-GD TCR CAR further comprises a nucleic acid sequence encoding a VH3-23 signal peptide. In further embodiments, the VH3-23 signal peptide comprises the amino acid sequence of SEQ ID NO: 2. In yet further embodiments, the nucleic acid sequence encoding the VH3-23 signal peptide comprises SEQ ID NO: 10.

In some embodiments, the transmembrane domain comprises a CD8 alpha chain hinge and transmembrane domain. In some embodiments, the CD8 alpha chain hinge and transmembrane domain comprise the amino acid sequence of SEQ ID NO: 6. In yet further embodiments, the CD8 alpha chain hinge and transmembrane domain are encoded by a nucleic acid sequence comprising SEQ ID NO: 14.

In some embodiments, the isolated nucleic acid sequence encoding an anti-GD TCR CAR further comprises a nucleic acid sequence encoding a peptide linker. In some embodiments, the peptide linker comprises the amino acid sequence of SEQ ID NO: 4. In further embodiments, the nucleic acid sequence encoding the peptide linker comprises SEQ ID NO: 12.

In some embodiments, the intracellular signaling domain comprises a nucleic acid sequence encoding a CD137 intracellular domain. In further embodiments, the CD137 intracellular domain comprises the amino acid sequence of SEQ ID NO: 7. In yet further embodiments, the nucleic acid sequence encoding the CD137 intracellular domain comprises SEQ ID NO: 15.

In some embodiments, the intracellular signaling domain comprises a nucleic acid sequence encoding a CD3 zeta signaling domain. In further embodiments, the CD3 zeta signaling domain comprises an amino acid sequence of SEQ ID NO: 8. In yet further embodiments, the nucleic acid sequence encoding the CD3 zeta signaling domain comprises SEQ ID NO: 16.

Provided is a vector comprising the isolated nucleic acid sequence of any one of the previous embodiments. In further embodiments, the vector is a lentiviral vector. In yet further embodiments, the vector is a RNA vector.

Also provided is an isolated anti-GD TCR CAR comprising an extracellular domain comprising an anti-GD TCR or fragment thereof, a transmembrane domain, and an intracellular signaling domain. In some embodiments, the anti-GD TCR or fragment thereof comprises a light chain comprising the amino acid sequence of SEQ ID NO: 3 or a heavy chain comprising the amino acid sequence of SEQ ID NO:5.

Also provided is an anti-GD TCR CAR comprising an extracellular domain comprising an anti-GD TCR or fragment thereof, a transmembrane domain, and an intracellular signaling domain, wherein the anti-GD TCR or fragment thereof binds to the same epitope as an anti-GD TCR or fragment thereof comprising a light chain comprising the amino acid sequence of SEQ ID NO: 3 or a heavy chain comprising the amino acid sequence of SEQ ID NO: 5. Also provided is an anti-GD TCR CAR comprising an extracellular domain comprising an anti-GD TCR or fragment thereof, a transmembrane domain, and an intracellular signaling domain, wherein the anti-GD TCR or fragment thereof binds to the same epitope as an anti-GD TCR that blocks an anti-GD TCR or fragment thereof comprising a light chain comprising the amino acid sequence of SEQ ID NO: 3 or a heavy chain comprising the amino acid sequence of SEQ ID NO: 5.

In some embodiments, the anti-GD TCR or fragment thereof of any of the previous embodiments further comprises a VH3-23 signal peptide. In some embodiments, the VH3-23 signal peptide comprises the amino acid sequence of SEQ ID NO:2. In further embodiments, the transmembrane domain comprises a CD8 alpha chain hinge and transmembrane domain. In yet further embodiments, the CD8 alpha chain hinge and transmembrane domain comprise SEQ ID NO: 6.

In some embodiments, the anti-GD TCR or fragment thereof of any of the previous embodiments further comprises a peptide linker. In further embodiments, the peptide linker comprises SEQ ID NO: 4.

In some embodiments, the intracellular signaling domain comprises a CD137 intracellular domain. In further embodiments, the CD137 intracellular domain comprises SEQ ID NO: 7.

In some embodiments, the intracellular signaling domain comprises a CD3 zeta signaling domain. In further embodiments, the CD3 zeta signaling domain comprises an amino acid sequence of SEQ ID NO:8.

Provided is a genetically modified cell comprising the anti-GD TCR CAR of any one of the previous embodiments. In some embodiments, the cell expresses the anti-GD TCR CAR and has high affinity for GD T cells. In further embodiments, the cell expresses the anti-GD TCR CAR and induces killing of GD T cells or cells expressing GD TCR. In yet further embodiments, the cell is selected from the group consisting of a helper cell, a cytotoxic T cell, a memory T cell, regulatory T cell, a natural killer cell, a cytokine induced killer cell, a cell line thereof, a T memory stem cell and other effector cell. In yet further embodiments, the cell is derived from an induced pluripotent stem cell. In some embodiments, the cell is an allogeneic cell. In some embodiments, the cell is an allogeneic cell selected from the group consisting of a helper T cell, a cytotoxic T cell, a memory T cell, regulatory T cell, a natural killer cell, a cytokine induced killer cell, a cell line thereof, a T memory stem cell and other effector cell. In some embodiments, the allogeneic T cell has had an endogenous CD3 knocked out. In some embodiments, the allogeneic T cell has had an endogenous TCR knocked out. In further embodiments, the allogeneic T cell has had an endogenous MHCI or MHCII or beta 2 microglobulin (B2M) knocked out. In some embodiments, both an endogenous CD3 and an endogenous MHCI of the cell have been knocked out. A variety of methods can be used to knock out expression of a gene to render the cell allogeneic, for example, without limitation, a CRISPR/CAS system, a transcription-activator like effector nuclease (TALEN), a zinc finger endonuclease (ZFN) or a viral system. In some preferred embodiments, an endogenous CD3 and an endogenous MHCI of the cell has been knocked out using a CRISPR/CAS system.

Also provided is a method for treating a GD T cell related disease in a subject, the method comprising: administering to the subject an effective amount of a genetically modified T cell comprising an isolated nucleic acid sequence encoding an anti-GD TCR CAR, wherein the isolated nucleic acid sequence comprises a nucleic acid sequence encoding an extracellular domain comprising an anti-GD TCR or fragment thereof, a nucleic acid sequence encoding a transmembrane domain, and a nucleic acid sequence encoding an intracellular signaling domain, thereby treating the GD T cell related disease in the subject. In some embodiments, the GD T cell related disease is an inflammatory or autoimmune disease selected from the group consisting of juvenile idiopathic arthritis, Behcet's disease, alopecia areata, systemic sclerosis, atherosclerosis, psoriasis, myositis, rheumatoid arthritis, inflammatory bowel disease, multiple sclerosis, type I diabetes, ankylosing spondylitis, autoimmune uveitis, Sjogren's syndrome, systemic lupus, and chronic cutaneous lupus. In some embodiments, the GD T cell related disease is a GD T cell lymphoma (GDTCL). In some embodiments, the GD T cell related disease is a GD TCR-expressing T cell lymphoma. In further embodiments, the subject is a human. In yet further embodiments, the modified T cell targets a GD T cell or a cell expressing GD TCR.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 6A illustrates a panel of histograms that show binding of HP (left) and IMMU510 (right) after preincubation with various amounts of the other clone (IMMU510 left, or HP right, respectively). Preincubation with one of the clones resulted in reduced binding of the other. FIG. 6B illustrates a bar graph where MFI after preincubation (setup as in FIG. 6A) was compared to staining without preincubation and is expressed as blocking percentage. Preincubation with IMMU510 blocked binding of HP (left) and preincubation with HP blocked binding of IMMU510 (right).

FIG. 8A is a panel of flow cytometry plots showing that anti-CD19 CAR treated mice developed leukemia with Loucy T cells being detectable in the peripheral circulation (left), while anti-GD TCR CAR treated mice did not demonstrate detectable Loucy GD T cells. FIG. 8B is a plot showing the quantification of GD T cells in the peripheral circulation (day 47, blood), demonstrating eradication of Loucy GD T cells by anti-GD CAR T cells (p=0.0072). Each dot represents one mouse.

FIGS. 9A-9C illustrate that the anti-GD TCR clone (called HP or 5A6.E9) used in the anti-GD TCR CAR, and another anti-GD TCR clone (called F2) bind to the same or overlapping epitope on the GD TCR. Primary human T cells (after expansion with anti CD3 and anti CD28 beads, therefore, the percentage of GD T cells is lower than prior to activation) were stained with 5A6.E9-AF647 or 11F2-PE. Staining was compared to fluorescence minus one (FMO) samples that were unstained. FSC-H represents the size of the cells. FIG. 9A shows that the percentage of 5A6.E9 stained cells did not change when co-stained with 11F2 (0.42 vs 0.43%). FIG. 9B shows that the binding of 11F2 was almost completely abolished by co-incubation with 5A6.E9, indicating that the 2 clones bind to the same or overlapping epitopes. FIG. 9C shows that when displaying both the PE and the AF647 channel, staining with 11F2 resulted in a discrete PE positive population (left panel), while co-incubation of the cells with both 11F2 and 5A6.E9 resulted in disappearance of the PE positive population (right panel).

DETAILED DESCRIPTION

Figure 1:
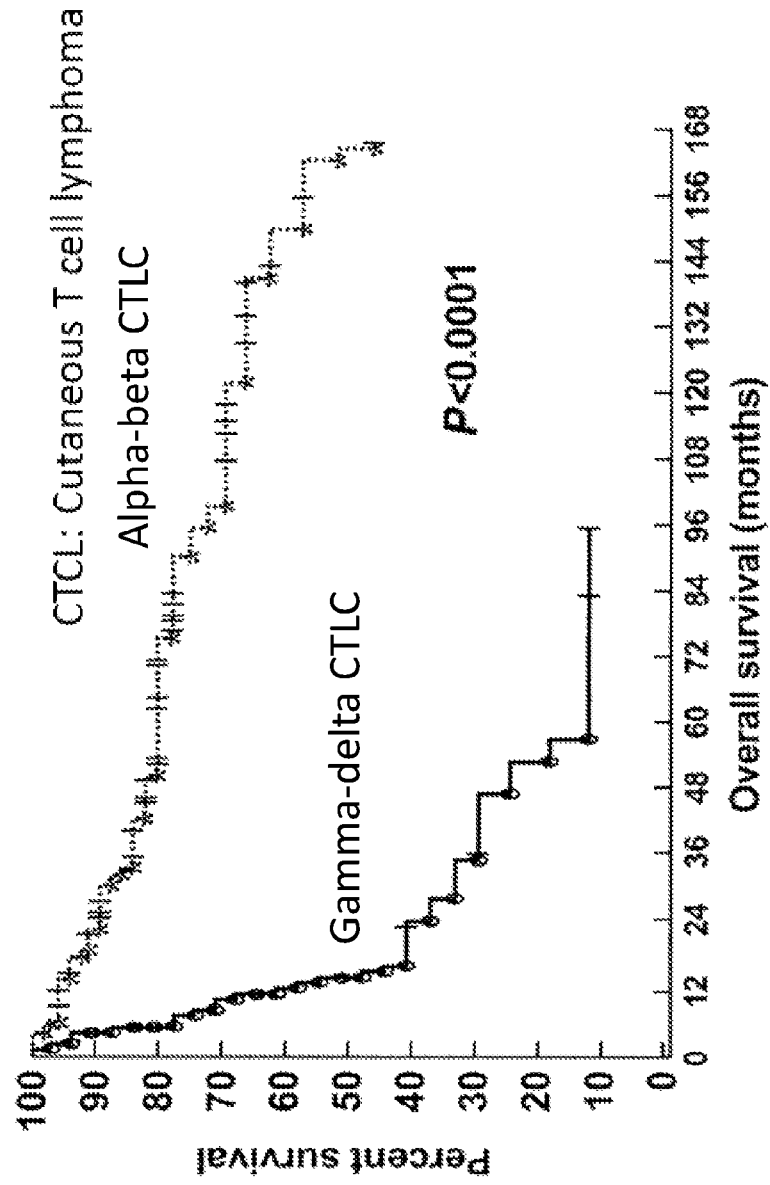
FIG. 1 is a graph showing that cutaneous GD T cell lymphomas have a poor prognosis. The Kaplan and Meier plots of patients with cutaneous T-cell lymphoma depict the survival of individuals with cutaneous T-cell lymphoma according to T-cell-receptor immunophenotype. A comparison was made between patients with alpha-beta (dotted line) and gamma-delta (solid line) cutaneous T-cell lymphomas. Significance was determined by the log-rank test (Toro et al., Blood 2003; 101:3407-3412).

The invention includes compositions comprising a chimeric antigen receptor (CAR) specific for GD TCR (anti-GD TCR CAR), vectors comprising the same, compositions comprising anti-GD TCR CAR vectors packaged in viral particles, and recombinant T cells comprising the anti-GD TCR CAR. The invention also includes methods of making a genetically modified T cell expressing an anti-GD TCR CAR.

The present invention also relates generally to the use of T cells engineered to express an anti-GD TCR CAR to treat a disease associated with GD T cells. In one embodiment, the T cells expressing the anti-GD TCR CAR of the invention specifically bind to and kill GD T cells, but not other T cells (such as but not limited to alpha beta T cells that do not express GD TCR).

Definitions

Unless defined otherwise, all technical and scientific terms used herein have the same meaning as commonly understood by one of ordinary skill in the art to which the invention pertains. Although any methods and materials similar or equivalent to those described herein can be used in the practice of and/or for the testing of the present invention, the preferred materials and methods are described herein. In describing and claiming the present invention, the following terminology will be used according to how it is defined, where a definition is provided.

It is also to be understood that the terminology used herein is for the purpose of describing particular embodiments only, and is not intended to be limiting.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, in some instances ±5%, in some instances ±1%, and in some instance ±0.1% from the specified value, as such variations are appropriate to perform the disclosed methods.

The term "antibody," as used herein, refers to an immunoglobulin molecule binds with an antigen. Antibodies can be intact immunoglobulins derived from natural sources or from recombinant sources and can be immunoreactive portions of intact immunoglobulins. Antibodies are typically tetramers of immunoglobulin molecules. The antibody in the present invention may exist in a variety of forms where the antibody is expressed as part of a contiguous polypeptide chain including, for example, a single domain antibody fragment (sdAb), a single chain antibody (scFv) and a humanized antibody (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, NY; Houston et al., 1988, Proc. Natl. Acad. Sci. USA 85:5879-5883; Bird et al., 1988, Science 242:423-426).

The term "high affinity" as used herein refers to high specificity in binding or interacting or attraction of one molecule to a target molecule.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of more than one gene and that these nucleotide sequences are arranged in various combinations to encode polypeptides that elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "limited toxicity" as used herein, refers to the peptides, polynucleotides, cells and/or antibodies of the invention manifesting a lack of substantially negative biological effects, anti-tumor effects, or substantially negative physiological symptoms toward a healthy cell, non-tumor cell, non-diseased cell, non-target cell or population of such cells either in vitro or in vivo.

The term "autoimmune disease" as used herein is defined as a disorder or condition that results from an antibody mediated autoimmune response against autoantigens. An autoimmune disease results in the production of autoantibodies that are inappropriately produced and/or excessively produced to a self-antigen or autoantigen.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

As used herein, the term "conservative sequence modifications" is intended to refer to amino acid modifications that do not significantly affect or alter the binding characteristics of the antibody containing the amino acid sequence. Such conservative modifications include amino acid substitutions, additions and deletions. Modifications can be introduced into an antibody of the invention by standard techniques known in the art, such as site-directed mutagenesis and PCR-mediated mutagenesis. Conservative amino acid substitutions are ones in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Thus, for example, one or more amino acid residues within the extracellular regions of the CAR of the invention can be replaced with other amino acid residues having a similar side chain or charge and the altered CAR can be tested for the ability to bind GD T cells using the functional assays described herein.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

The term "CRISPR/CAS," "clustered regularly interspaced short palindromic repeats system," or "CRISPR" refers to DNA loci containing short repetitions of base sequences. Each repetition is followed by short segments of spacer DNA from previous exposures to a virus. Bacteria and archaea have evolved adaptive immune defenses termed CRISPR-CRISPR-associated (Cas) systems that use short RNA to direct degradation of foreign nucleic acids. In bacteria, the CRISPR system provides acquired immunity against invading foreign DNA via RNA-guided DNA cleavage.

In the type II CRISPR/Cas system, short segments of foreign DNA, termed "spacers" are integrated within the CRISPR genomic loci are transcribed and processed into short CRISPR RNA (crRNA). These crRNAs anneal to trans-activating crRNAs (tracrRNAs) and direct sequence-specific cleavage and silencing of pathogenic DNA by Cas proteins. Recent work has shown that target recognition by the Cas9 protein requires a "seed" sequence within the crRNA and a conserved dinucleotide-containing protospacer adjacent motif (PAM) sequence upstream of the crRNA-binding region.

To direct Cas9 to cleave sequences of interest, crRNA-tracrRNA fusion transcripts, hereafter referred to as "guide RNAs" or "gRNAs" may be designed, from human U6 polymerase III promoter. CRISPR/Cas mediated genome editing and regulation, highlighted its transformative potential for basic science, cellular engineering and therapeutics.

The term "CRISPRi" refers to a CRISPR system for sequence specific gene repression or inhibition of gene expression at the transcriptional level.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

"Effective amount" or "therapeutically effective amount" are used interchangeably herein, and refer to an amount of a compound, formulation, material, or composition, as described herein effective to achieve a particular biological result. Such results may include, but are not limited to, the inhibition of virus infection as determined by any means suitable in the art.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by a promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes), retrotransposons (e.g. piggyback, sleeping beauty), and viruses (e.g., lentiviruses, retroviruses, adenoviruses, and adeno-associated viruses) that incorporate the recombinant polynucleotide.

"Homologous" as used herein, refers to the subunit sequence identity between two polymeric molecules, e.g., between two nucleic acid molecules, such as, two DNA molecules or two RNA molecules, or between two polypeptide molecules. When a subunit position in both of the two molecules is occupied by the same monomeric subunit; e.g., if a position in each of two DNA molecules is occupied by adenine, then they are homologous at that position. The homology between two sequences is a direct function of the number of matching or homologous positions; e.g., if half (e.g., five positions in a polymer ten subunits in length) of the positions in two sequences are homologous, the two sequences are 50% homologous; if 90% of the positions (e.g., 9 of 10), are matched or homologous, the two sequences are 90% homologous.

"Identity" as used herein refers to the subunit sequence identity between two polymeric molecules particularly between two amino acid molecules, such as, between two polypeptide molecules. When two amino acid sequences have the same residues at the same positions; e.g., if a position in each of two polypeptide molecules is occupied by an Arginine, then they are identical at that position. The identity or extent to which two amino acid sequences have the same residues at the same positions in an alignment is often expressed as a percentage. The identity between two amino acid sequences is a direct function of the number of matching or identical positions; e.g., if half (e.g., five positions in a polymer ten amino acids in length) of the positions in two sequences are identical, the two sequences are 50% identical; if 90% of the positions (e.g., 9 of 10), are matched or identical, the two amino acids sequences are 90% identical.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Intracellular domain" refers to a portion or region of a molecule that resides inside a cell.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

"Parenteral" administration of an immunogenic composition includes, e.g., subcutaneous (s.c.), intravenous (i.v.), intramuscular (i.m.), or intrasternal injection, or infusion techniques.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "proinflammatory cytokine" refers to a cytokine or factor that promotes inflammation or inflammatory responses. Examples of proinflammatory cytokines include, but are not limited to, chemokines (CCL, CXCL, CX3CL, XCL), interleukins (such as, IL-1, IL-2, IL-3, IL-5, IL-6, IL-7, IL-9, IL10 and IL-15), interferons (IFNγ), and tumor necrosis factors (TNFα and TNFβ).

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

A "signal transduction pathway" refers to the biochemical relationship between a variety of signal transduction molecules that play a role in the transmission of a signal from one portion of a cell to another portion of a cell. The phrase "cell surface receptor" includes molecules and complexes of molecules capable of receiving a signal and transmitting signal across the membrane of a cell.

"Signaling domain" refers to the portion or region of a molecule that recruits and interacts with specific proteins in response to an activating signal.

The term "subject" is intended to include living organisms in which an immune response can be elicited (e.g., mammals).

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cells that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

"Transmembrane domain" refers to a portion or a region of a molecule that spans a lipid bilayer membrane.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, lentiviral vectors, and the like.

By the term "specifically binds," as used herein, is meant an antibody, or a ligand, which recognizes and binds with a cognate binding partner (e.g., a stimulatory and/or costimulatory molecule present on a T cell) protein present in a sample, but which antibody or ligand does not substantially recognize or bind other molecules in the sample.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an WIC Class I molecule loaded with a peptide, an anti-CD3 antibody, a superagonist anti-CD28 antibody, and a superagonist anti-CD2 antibody.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

Chimeric Antigen Receptor (CAR)

The present invention is based on the discovery that chimeric receptors can be used to target gamma delta T cell receptor (GD TCR). The invention includes compositions comprising at least one chimeric antigen receptor (CAR) specific for an antigen binding domain (GD TCR), vectors comprising the same, compositions comprising anti-GD TCR CAR vectors packaged in viral particles, and recombinant T cells or other effector cells comprising the anti-GD TCR CAR of this invention. In some embodiments, the anti-GD TCR is specific for an epitope on the GD TCR. In some embodiments, the epitope is on the antigen binding domain of the GD TCR. The invention also includes methods of making a genetically modified T cell expressing an anti-GD TCR CAR wherein the expressed CAR comprises an extracellular domain that binds to GD T cells or to cells expressing a GD TCR.

Example of CARs are described in U.S. Pat. Nos. 8,911,993, 8,906,682, 8,975,071, 8,916,381, 9,102,760, 9,101,584, and 9,102,761, all of which are incorporated herein by reference in their entireties.

The present invention includes a method for treating GD T cell-mediated diseases. The invention includes a method for efficiently targeting and killing the pathogenic GD T cells by targeting the GD TCR using an anti-GD TCR CAR.

The present invention encompasses a recombinant DNA construct comprising nucleic acid sequences that encode an extracellular domain comprising an antibody anti-GD TCR or a fragment thereof, wherein the sequence of anti-GD TCR or fragment thereof is operably linked to a nucleic acid sequence encoding an intracellular signaling domain. The intracellular signaling domain or otherwise the cytoplasmic domain comprises, a costimulatory signaling region. The costimulatory signaling region refers to a portion of the CAR comprising the intracellular domain of a costimulatory molecule. Costimulatory molecules are cell surface molecules that are required for an efficient T cell activation.

In one aspect, the invention includes an isolated nucleic acid sequence encoding a chimeric antigen receptor (CAR), wherein the isolated nucleic acid sequence comprises a nucleic acid sequence encoding an extracellular domain comprising an anti-GD TCR or fragment thereof, a nucleic acid sequence encoding a transmembrane domain, and a nucleic acid sequence encoding an intracellular signaling domain.

Antigen Binding Domain

In one embodiment, the CAR of the invention comprises an antigen binding domain that binds to a GD TCR on a T cell or on a cell expressing a GD TCR.

The choice of antigen binding domain depends upon the type and number of antigens that are present in a protein aggregate or on the surface of a target cell. For example, the antigen binding domain may be chosen to recognize an antigen that acts as a cell surface marker on a target cell associated with a particular disease state (e.g a disease related to GD T cells).

The antigen binding domain can include any domain that binds to the antigen and may include, but is not limited to, a monoclonal antibody, a polyclonal antibody, a synthetic antibody, a human antibody, a humanized antibody, a non-human antibody, and any fragment thereof. Thus, in one embodiment, the antigen binding domain portion comprises a mammalian antibody or a fragment thereof. In another embodiment, the antigen binding domain is selected from the group consisting of a Fab fragment, a F(ab')$_2$ fragment, a Fv fragment, and a single chain Fv (scFv).

In some instances, the antigen binding domain is derived from the same species in which the CAR will ultimately be used in. For example, for use in humans, it the antigen binding domain of the CAR comprises a human antibody, a humanized antibody, or a fragment thereof.

In some aspects of the invention, the antigen binding domain is operably linked to another domain of the CAR, such as the transmembrane domain or the intracellular domain, for expression in the cell. In one embodiment, a nucleic acid encoding the antigen binding domain is operably linked to a nucleic acid encoding a transmembrane domain and a nucleic acid encoding an intracellular domain.

In one embodiment, the antigen binding domain of the CAR is an anti-GD TCR antibody or fragment thereof. In one embodiment, the anti-GD TCR CAR comprises an amino acid sequence of SEQ ID NO: 1. In one embodiment, the nucleic acid sequence encoding the anti-GD TCR CAR comprises SEQ ID NO: 9.

In another embodiment, the anti-GD TCR or fragment thereof comprises at least one nucleic acid sequence encoding a light chain with an amino acid sequence of SEQ ID NO: 3 or a heavy chain with an amino acid sequence of SEQ ID NO:5. In yet another embodiment, the anti-GD TCR or fragment thereof comprises at least a light chain encoded by a nucleic acid sequence of SEQ ID NO: 11 or a heavy chain encoded by a nucleic acid sequence of SEQ ID NO: 13.

Also provided is an anti-GD TCR CAR comprising an extracellular domain comprising an anti-GD TCR or fragment thereof, a transmembrane domain, and an intracellular signaling domain, wherein the anti-GD TCR or fragment thereof binds to the same epitope as an anti-GD TCR or fragment thereof comprising a light chain comprising the amino acid sequence of SEQ ID NO: 3 or a heavy chain comprising the amino acid sequence of SEQ ID NO: 5. In further embodiments, the anti-GD TCR or fragment thereof binds to the same epitope as an anti-GD TCR that blocks an anti-GD TCR or fragment thereof comprising a light chain comprising the amino acid sequence of SEQ ID NO: 3 or a heavy chain comprising the amino acid sequence of SEQ ID NO: 5.

Human Antibodies

It may be preferable to use human antibodies or fragments thereof when using the antigen binding domain of a CAR. Completely human antibodies are particularly desirable for therapeutic treatment of human subjects. Human antibodies can be made by a variety of methods known in the art including phage display methods using antibody libraries derived from human immunoglobulin sequences, including improvements to these techniques. See, also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. For example, it has been described that the homozygous deletion of the antibody heavy chain joining region (JH) gene in chimeric and germ-line mutant mice results in complete inhibition of endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Antibodies directed against the target of choice can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies, including, but not limited to, IgG1 (gamma 1) and IgG3. For an overview of this technology for producing human antibodies, see, Lonberg and Huszar (Int. Rev. Immunol., 13:65-93 (1995)). For a detailed discussion of this technology for producing human antibodies and human monoclonal antibodies and protocols for producing such antibodies, see, e.g., PCT Publication Nos. WO 98/24893, WO 96/34096, and WO 96/33735; and U.S. Pat. Nos. 5,413,923; 5,625,126; 5,633,425; 5,569,825; 5,661,016; 5,545,806; 5,814,318; and 5,939,598, each of which is incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above. For a specific discussion of transfer of a human germ-line immunoglobulin gene array in germ-line mutant mice that will result in the production of human antibodies upon antigen challenge see, e.g., Jakobovits et al., 1993, Proc. Natl. Acad. Sci. USA, 90:2551; Jakobovits et al., 1993, Nature, 362:255-258; Bruggermann et al., 1993, Year in Immunol., 7:33; and Duchosal et al., 1992, Nature, 355:258.

Human antibodies can also be derived from phage-display libraries (Hoogenboom et al., J. Mol. Biol., 227:381 (1991); Marks et al., J. Mol. Biol., 222:581-597 (1991); Vaughan et al., Nature Biotech., 14:309 (1996)). Phage display technology (McCafferty et al., Nature, 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of unimmunized mice. A repertoire of V genes from unimmunized human donors can be constructed and antibodies to a diverse array of antigens (including self-antigens) can be isolated essentially following the techniques described by Marks et al., J. Mol. Biol., 222:581-597 (1991), or Griffith et al., EMBO J., 12:725-734 (1993). See, also, U.S. Pat. Nos. 5,565,332 and 5,573,905, each of which is incorporated herein by reference in its entirety.

Human antibodies may also be generated by in vitro activated B cells (see, U.S. Pat. Nos. 5,567,610 and 5,229,275, each of which is incorporated herein by reference in its entirety). Human antibodies may also be generated in vitro using hybridoma techniques such as, but not limited to, that described by Roder et al. (Methods Enzymol., 121:140-167 (1986)).

Humanized Antibodies

Alternatively, in some embodiments, a non-human antibody can be humanized, where specific sequences or regions of the antibody are modified to increase similarity to an antibody naturally produced in a human. For instance, in the present invention, the antibody or fragment thereof may comprise a non-human mammalian scFv. In one embodiment, the antigen binding domain portion is humanized.

A humanized antibody can be produced using a variety of techniques known in the art, including but not limited to, CDR-grafting (see, e.g., European Patent No. EP 239,400; International Publication No. WO 91/09967; and U.S. Pat. Nos. 5,225,539, 5,530,101, and 5,585,089, each of which is incorporated herein in its entirety by reference), veneering or resurfacing (see, e.g., European Patent Nos. EP 592,106 and EP 519,596; Padlan, 1991, Molecular Immunology, 28(4/5):489-498; Studnicka et al., 1994, Protein Engineering, 7(6):805-814; and Roguska et al., 1994, PNAS, 91:969-973, each of which is incorporated herein by its entirety by reference), chain shuffling (see, e.g., U.S. Pat. No. 5,565,332, which is incorporated herein in its entirety by reference), and techniques disclosed in, e.g., U.S. Patent Application Publication No. US2005/0042664, U.S. Patent Application Publication No. US2005/0048617, U.S. Pat. Nos. 6,407,213, 5,766,886, International Publication No. WO 9317105, Tan et al., J. Immunol., 169:1119-25 (2002), Caldas et al., Protein Eng., 13(5):353-60 (2000), Morea et al., Methods, 20(3):267-79 (2000), Baca et al., J. Biol. Chem., 272(16):10678-84 (1997), Roguska et al., Protein Eng., 9(10):895-904 (1996), Couto et al., Cancer Res., 55 (23 Supp):5973s-5977s (1995), Couto et al., Cancer Res., 55(8):1717-22 (1995), Sandhu J S, Gene, 150(2):409-10 (1994), and Pedersen et al., J. Mol. Biol., 235(3):959-73 (1994), each of which is incorporated herein in its entirety by reference. Often, framework residues in the framework regions will be substituted with the corresponding residue from the CDR donor antibody to alter, preferably improve, antigen binding. These framework substitutions are identified by methods well-known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature, 332:323, which are incorporated herein by reference in their entireties.)

A humanized antibody has one or more amino acid residues introduced into it from a source which is nonhuman. These nonhuman amino acid residues are often referred to as "import" residues, which are typically taken from an "import" variable domain. Thus, humanized antibodies comprise one or more CDRs from nonhuman immunoglobulin molecules and framework regions from human. Humanization of antibodies is well-known in the art and can essentially be performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody, i.e., CDR-grafting (EP 239,400; PCT Publication No. WO 91/09967; and U.S. Pat. Nos. 4,816,567; 6,331,415; 5,225,539; 5,530,101; 5,585,089; 6,548,640, the contents of which are incorporated herein by reference herein in their entirety). In such humanized chimeric antibodies, substantially less than an intact human variable domain has been substituted by the corresponding sequence from a nonhuman species. In practice, humanized antibodies are typically human antibodies in which some CDR residues and possibly some framework (FR) residues are substituted by residues from analogous sites in rodent antibodies. Humanization of antibodies can also be achieved by veneering or resurfacing (EP 592,106; EP 519,596; Padlan, 1991, Molecular Immunology, 28(4/5):489-498; Studnicka et al., Protein Engineering, 7(6):805-814 (1994); and Roguska et al., PNAS, 91:969-973 (1994)) or chain shuffling (U.S. Pat. No. 5,565,332), the contents of which are incorporated herein by reference herein in their entirety.

The choice of human variable domains, both light and heavy, to be used in making the humanized antibodies is to reduce antigenicity. According to the so-called "best-fit" method, the sequence of the variable domain of a rodent antibody is screened against the entire library of known human variable-domain sequences. The human sequence which is closest to that of the rodent is then accepted as the human framework (FR) for the humanized antibody (Sims et al., J. Immunol., 151:2296 (1993); Chothia et al., J. Mol. Biol., 196:901 (1987), the contents of which are incorporated herein by reference herein in their entirety). Another method uses a particular framework derived from the consensus sequence of all human antibodies of a particular subgroup of light or heavy chains. The same framework may be used for several different humanized antibodies (Carter et al., Proc. Natl. Acad. Sci. USA, 89:4285 (1992); Presta et al., J. Immunol., 151:2623 (1993), the contents of which are incorporated herein by reference herein in their entirety).

Antibodies can be humanized that retain high affinity for the target antigen and that possess other favorable biological properties. According to one aspect of the invention, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind the target antigen. In this way, FR residues can be selected and combined from the recipient and import sequences so that the desired antibody characteristic, such as increased affinity for the target antigen, is achieved. In general, the CDR residues are directly and most substantially involved in influencing antigen binding.

A humanized antibody retains a similar antigenic specificity as the original antibody. However, using certain methods of humanization, the affinity and/or specificity of binding of the antibody to the target antigen may be increased using methods of "directed evolution," as described by Wu et al., J. Mol. Biol., 294:151 (1999), the contents of which are incorporated herein by reference herein in their entirety.

T Cell Signaling Molecule

The present invention includes methods and compositions that include a T cell signaling molecule, as well as the peptide described herein. Examples of a T cell signaling molecule include, but are not limited to, an exogenous TCR, such as a wildtype TCR, a high affinity TCR, or a chimeric TCR with affinity for a target cell, a co-stimulatory T cell molecule, and a chimeric co-stimulatory T cell molecule.

T Cell Receptor

The present invention includes a CAR targeting a T cell receptor (TCR) (i.e. anti-GD TCR CAR).

A TCR is a complex of membrane proteins that participate in the activation of T cells in response to the presentation of antigen. Stimulation of the TCR is triggered by major histocompatibility complex molecules (MHC) on antigen presenting cells that present antigen peptides to the T cells and bind to the TCR complexes to induce a series of intracellular signaling cascades.

In embodiments that include a TCR as the T cell signaling molecule, the TCR is generally composed of six different membrane bound chains that form the TCR heterodimer responsible for ligand recognition. TCRs exist in alpha/beta and gamma/delta forms, which are structurally similar but have distinct anatomical locations and functions.

Each chain is composed of two extracellular domains, a variable and constant domain.

Each of the constant and variable domains may include an intra-chain disulfide bond. In one embodiment, TCR comprises at least one disulfide bond. The variable domains include the highly polymorphic loops analogous to the complementarity determining regions (CDRs) of antibodies. The diversity of TCR sequences is generated via somatic rearrangement of linked variable (V), diversity (D), joining (J), and constant genes.

Functional alpha and gamma chain polypeptides are formed by rearranged V-J-C regions, whereas beta and delta chains consist of V-D-J-C regions. The extracellular constant domain includes a membrane proximal region and an immunoglobulin region.

In one embodiment, the anti-GD TCR of the present invention targets a GD TCR. The targeted GD TCR may be an antigen associated with a particular disease state such as inflammatory, autoimmune disease and cancer. In some embodiments, the inflammatory and autoimmune disease is juvenile idiopathic arthritis, Behcet's disease, alopecia areata, systemic sclerosis, atherosclerosis, psoriasis, myositis, rheumatoid arthritis, inflammatory bowel disease, multiple sclerosis, type I diabetes, ankylosing spondylitis, autoimmune uveitis, Sjogren's syndrome, systemic lupus, and chronic cutaneous lupus. In other embodiments, the cancer is a GD T cell lymphoma (GDTCL).

In some instances, it is beneficial that the antibody anti-GD TCR is derived from the same species in which the anti-GD TCR CAR will ultimately be used.

Transmembrane Domain

In one embodiment, the anti-GD TCR CAR comprises a transmembrane domain, such as, but not limited to, a human T cell surface glycoprotein CD8 alpha chain hinge and/or transmembrane domain (amino acids 136-203 of the human T cell surface glycoprotein CD8 alpha chain, e.g. TTTPAPRPPTPAPTIASQPLSLRPEACRPAAGGAVHTRGLD-FACDIYIWAPLAG TCGVLLLSLVITLYC (SEQ ID NO: 17)). The human CD8 chain hinge and/or transmembrane domain provides cell surface presentation of the GD TCR.

With respect to the transmembrane domain, in various embodiments, the anti-GD TCR CAR comprises a transmembrane domain that is fused to the extracellular domain of the anti-GD TCR CAR. In one embodiment, the anti-GD TCR CAR comprises a transmembrane domain that naturally is associated with one of the domains in the anti-GD TCR CAR. In some instances, the transmembrane domain is be selected or modified by amino acid substitution to avoid binding to the transmembrane domains of the same or different surface membrane proteins in order to minimize interactions with other members of the receptor complex.

The transmembrane domain may be derived either from a natural or from a synthetic source. When the source is natural, the domain may be derived from any membrane-bound or transmembrane protein. In one embodiment, the transmembrane domain may be synthetic, in which case it will comprise predominantly hydrophobic residues such as leucine and valine. In one aspect a triplet of phenylalanine, tryptophan and valine will be found at each end of a synthetic transmembrane domain. Optionally, a short oligo- or polypeptide linker, between 2 and 10 amino acids in length may form the linkage between the transmembrane domain and the cytoplasmic signaling domain of the anti-GD TCR CAR. A glycine-serine doublet provides a particularly suitable linker.

In some instances, a variety of human hinges can be employed as well including the human Ig (immunoglobulin) hinge.

Examples of the hinge and/or transmembrane domain include, but are not limited to, a hinge and/or transmembrane domain of an alpha, beta or zeta chain of a T-cell receptor, CD28, CD3 epsilon, CD45, CD4, CD5, CD8, CD9, CD16, CD22, CD33, CD37, CD64, CD80, CD86, CD134, CD137, CD154, KIR, OX40, CD2, CD27, LFA-1 (CD11a, CD18), ICOS (CD278), 4-1BB (CD137), GITR, CD40, BAFFR, HVEM (LIGHTR), SLAMF7, NKp80 (KLRF1), CD160, CD19, IL2R beta, IL2R gamma, IL7R α, ITGA1, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and/or NKG2C.

In one embodiment, the nucleic acid sequence of the transmembrane domain encodes a CD8 alpha chain hinge and/or transmembrane domain. In another embodiment, the nucleic acid sequence of the CD8 alpha chain hinge and/or transmembrane domain encodes an amino acid sequence comprising SEQ ID NO: 6 or SEQ ID NO: 17.

In yet another embodiment, the transmembrane domain comprises a CD8 alpha chain hinge and/or transmembrane domain.

Cytoplasmic Domain

The cytoplasmic domain or otherwise the intracellular signaling domain of the anti-GD TCR CAR of the invention, is responsible for activation of at least one of the normal effector functions of the immune cell in which the anti-GD TCR CAR has been placed in.

The term "effector function" refers to a specialized function of a cell.

Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While the entire intracellular signaling domain can be employed, in many cases it is not necessary to use the entire domain. To the extent that a truncated portion of the intracellular signaling domain is used, such truncated portion may be used in place of the intact domain as long as it transduces the effector function signal.

The term "intracellular signaling domain" is thus meant to include any truncated portion of the intracellular domain sufficient to transduce the effector function signal.

Examples of intracellular signaling domains for use in the anti-GD TCR CAR of the invention include, but are not limited to, the cytoplasmic portion of the T cell receptor (TCR) and co-receptors that act in concert to initiate signal transduction following antigen receptor engagement, as well as any derivative or variant of these elements and any synthetic sequence that has the same functional capability.

It is well recognized that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory manner or in an inhibitory manner. Primary cytoplasmic signaling sequences that act in a stimulatory manner may contain signaling motifs which are known as immunoreceptor tyrosine-based activation motifs or ITAMs.

Examples of the intracellular signaling domain includes a fragment or domain from one or more molecules or receptors including, but are not limited to, CD3 zeta, CD3 gamma, CD3 delta, CD3 epsilon, CD86, common FcR gamma, FcR beta (Fc Epsilon Rib), CD79a, CD79b, Fcgamma RIIa, DAP10, DAP12, T cell receptor (TCR), CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, a ligand that specifically binds with CD83, CDS, ICAM-1, GITR, BAFFR, HVEM (LIGHTR), SLAMF7, NKp80 (KLRF1), CD127, CD160, CD19, CD4, CD8alpha, CD8beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, NKG2D, other co-stimulatory molecules described herein, any derivative, variant, or fragment thereof, any synthetic sequence of a co-stimulatory molecule that has the same functional capability, and any combination thereof.

In a preferred embodiment, the intracellular signaling domain of the anti-GD TCR CAR comprises the CD3-zeta signaling domain by itself or in combination with any other desired cytoplasmic domain(s) useful in the context of the anti-GD TCR CAR of the invention. For example, the intracellular signaling domain of the anti-GD TCR CAR can comprise a CD3 zeta chain portion and a costimulatory signaling region. The costimulatory signaling region refers to a portion of the anti-GD TCR CAR comprising the intracellular domain of a costimulatory molecule. A costimulatory molecule is a cell surface molecule other than an antigen receptor or its ligands that is required for an efficient response of lymphocytes to an antigen.

In yet another embodiment, the intracellular signaling domain encodes a CD137 intracellular domain (KRGRKKLLY-IFKQPFMRPVQTTQEEDGCSCRFPEEEEGGCEL (SEQ ID NO: 7)). In another embodiment, the nucleic acid sequence encoding the CD137 intracellular domain comprises SEQ ID NO: 15. In still another embodiment, the CD137 intracellular domain comprises a human T-cell surface glycoprotein CD3 zeta chain isoform 3 intracellular domain (human CD247, (CD3zeta)).

The human intracellular CD3 zeta domain provides stimulatory intracellular signaling upon binding of the anti-GD TCR CAR to the GD TCR, without HLA restriction.

In another embodiment, the nucleic acid sequence of the intracellular signaling domain comprises a nucleic acid sequence encoding a CD3 zeta signaling domain. In another embodiment, the nucleic acid sequence of the CD3 zeta signaling domain encodes an amino acid sequence comprising RVKFSRSADAPAYQQGQNQLYNELNLGRREEY-DVLDKRRGRDPEMGGKPR RKNPQEGLYNELQKDK-MAEAYSEIGMKGERRRGKGHDGLYQGLSTATKDT YDALHMQALPPR (SEQ ID NO: 8). In another embodiment, the nucleic acid sequence encoding the CD3 zeta signaling domain comprises SEQ ID NO: 16.

Other Domains

In another embodiment, the anti-GD TCR CAR and the nucleic acid encoding the anti-GD TCR CAR comprise a human VH3-23 signal peptide of SEQ ID NO: 2 (MEFGLSWLFLVAILKGVQC). In one embodiment, the isolated nucleic acid sequence encoding the anti-GD TCR CAR comprises a nucleic acid sequence encoding a VH3-23 signal peptide. In one embodiment, the nucleic acid sequence encoding the VH3-23 signal peptide comprises SEQ ID NO: 10 (ATGGAGTTTGGGCT-GAGCTGGCTTTTTCTTGTGGCTATTT-TAAAAGGTGTC CAGTGC). In some embodiments, the anti-GD TCR CAR comprises a CD8 alpha chain signal peptide.

In still another embodiment, the transmembrane domain comprises a CD8 alpha chain hinge and the transmembrane domain and CD8 alpha chain hinge comprise SEQ ID NO: 6. In another embodiment, the transmembrane domain comprises a CD8 alpha chain hinge and the transmembrane domain is encoded by a nucleic acid sequence comprising SEQ ID NO: 14.

In one embodiment, the isolated nucleic acid sequence encoding the anti-GD TCR CAR comprises a nucleic acid sequence encoding a peptide linker. In another embodiment, the nucleic acid sequence of peptide linker encodes an amino acid sequence comprising SEQ ID NO: 4. In another embodiment, the nucleic acid sequence encoding the peptide linker comprises SEQ ID NO: 12. In another embodiment, the cytoplasmic signaling sequences within the intracellular signaling domain of the anti-GD TCR CAR can be linked to each other in a random or specified order. Optionally, a short oligo- or polypeptide linker, for example, between 2 and 10 amino acids in length may form the linkage. A glycine-serine doublet is a particularly suitable linker.

In yet another embodiment, the anti-GD TCR CAR comprises a peptide linker. In still another embodiment, the peptide linker comprises SEQ ID NO:4, such as a human tumor necrosis factor receptor superfamily member 9 (also known as CD137 or 4-1BB ligand receptor) intracellular domain. The human intracellular CD137 domain provides co-stimulatory intracellular signaling upon binding to the GD TCR.

Any domains and/or fragments of the anti-GD TCR CAR, vector, and the promoter may be amplified by PCR or any other means known in the art.

Vector Comprising the Anti-GD TCR CAR

For proof of concept as to specificity and functionality, a $3^{rd}$ generation self-inactivating lentiviral vector plasmid can be used in which the expression of the CAR is regulated by the human elongation factor 1 alpha promoter. This results in stable (permanent) expression of the CAR in the host T cell. As an alternative approach, the encoding mRNA can be electroporated into the host cell, which would achieve the same therapeutic effect as the virally transduced T cells, but would not be permanent because the mRNA would dilute out with cell division.

In one aspect, the invention includes a vector comprising an isolated nucleic acid sequence encoding an anti-GD TCR CAR, wherein the isolated nucleic acid sequence comprises a nucleic acid sequence (for example, a human sequence) encoding an extracellular domain comprising an anti-GD TCR or fragment thereof, a nucleic acid sequence encoding a transmembrane domain, and a nucleic acid sequence encoding an intracellular signaling domain. In one embodiment, the vector comprises any of the isolated nucleic acid sequences encoding the anti-GD TCR CAR as described herein. In another embodiment, the vector comprises a plasmid vector, viral vector, retrotransposon (e.g. piggyback, sleeping beauty), site directed insertion vector (e.g. CRISPR, zn finger nucleases, TALEN), or suicide expression vector, or other known vector in the art.

All constructs disclosed herein comprising different antigens and fragments thereof can be used with 3rd generation lentiviral vector plasmids, other viral vectors, or RNA approved for use in humans. In one embodiment, the vector is a viral vector, such as a lentiviral vector. In another embodiment, the vector is a RNA vector.

Expression of the anti-GD TCR CAR in cells can be verified by sequencing. Expression of the full length anti-GD TCR CAR protein may be verified using immunoblot, immunohistochemistry, flow cytometry or other technology well known and available in the art.

The present invention therefore provides a vector in which DNA encoding the anti-GD TCR CAR of the present invention is inserted. Vectors, including those derived from retroviruses such as lentivirus, are suitable tools to achieve long-term gene transfer since they allow long-term, stable integration of a transgene and its propagation in daughter cells. Lentiviral vectors have the added advantage over vectors derived from onco-retroviruses, such as murine leukemia viruses, in that they can transduce non-proliferating cells, such as hepatocytes. They also have the added advantage of resulting in low immunogenicity in the subject into which they are introduced.

In brief summary, the expression of natural or synthetic nucleic acids encoding anti-GD TCR CARs is typically achieved by operably linking a nucleic acid encoding the anti-GD TCR CAR polypeptide or portions thereof to a promoter, and incorporating the construct into an expression vector. The vector is one generally capable of replication in a mammalian cell, and/or also capable of integration into the cellular genome of the mammal. Typical vectors contain transcription and translation terminators, initiation sequences, and promoters useful for regulation of the expression of the desired nucleic acid sequence.

The nucleic acid can be cloned into any number of different types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

The expression vector may be provided to a cell in the form of a viral vector. Viral vector technology is well known in the art and is described, for example, in Sambrook et al., 2012, MOLECULAR CLONING: A LABORATORY MANUAL, volumes 1-4, Cold Spring Harbor Press, NY), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

An example of a promoter is the immediate early cytomegalovirus (CMV) promoter sequence. This promoter sequence is a strong constitutive promoter sequence capable of driving high levels of expression of any polynucleotide sequence operatively linked thereto. However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the elongation factor-1α promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of an anti-GD TCR CAR polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assessed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al., 2012, MOLECULAR CLONING: A LABORATORY MANUAL, volumes 1-4, Cold Spring Harbor Press, NY).

Biological methods for introducing a polynucleotide of interest into a host cell include the use of DNA and RNA vectors. RNA vectors include vectors having a RNA promoter and/other relevant domains for production of a RNA transcript. Viral vectors, and especially retroviral vectors, have become the most widely used method for inserting genes into mammalian, e.g., human cells. Other viral vectors may be derived from lentivirus, poxviruses, herpes simplex virus, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, MO; dicetyl phosphate ("DCP") can be obtained from K & K Laboratories (Plainview, NY); cholesterol ("Chol") can be obtained from Calbiochem-Behring; dimyristyl phosphatidylglycerol ("DMPG") and other lipids may be obtained from Avanti Polar Lipids, Inc. (Birmingham, AL.). Stock solutions of lipids in chloroform or chloroform/methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Cells Comprising the Anti-GD TCR CAR

In another aspect, the invention includes a genetically modified cell, such as a helper T cell, a cytotoxic T cell, a memory T cell, regulatory T cell, gamma delta T cell, a natural killer cell, cytokine induced killer cell, a cell line thereof, a T memory stem cell, and other effector cell, comprising a chimeric antibody (anti-GD TCR CAR), wherein the anti-GD TCR CAR comprises an extracellular domain comprising an autoantigen or fragment thereof, a transmembrane domain, and an intracellular signaling domain. In one embodiment, the genetically modified cell comprises the anti-GD TCR CAR described herein. In another embodiment, the cell expresses the anti-GD TCR CAR. In this embodiment, the cell has a high affinity for GD TCRs. As a result, the cell can induce killing of GD T cells expressing the GD TCR.

In yet another aspect, the present invention provides immune effector cells (e.g., T cells, NK cells) that are engineered to contain one or more TCRs that direct the immune effector cells to GD T cell related diseases or cancer (GDTCL).

It is also useful for the T cell to have limited toxicity toward healthy cells and specificity to cells expressing other TCR (e.g. alpha beta T cells). Such specificity prevents or reduces off-target toxicity.

The invention includes T cells, such as primary cells, expanded T cells derived from primary T cells, T cells derived from stem cells differentiated in vitro, T cell lines such as Jurkat cells, other sources of T cells, combinations thereof, and other effector cells. For example, a transduced Jurkat cell line with a NFAT response element followed by GFP can be used to detect and isolate GD T cells and to clone the GD TCR specific antibody repertoire in a comprehensive and unbiased fashion.

Further assessment of efficacy and safety of the anti-GD TCR CAR can be performed, for example, as follows: Constructs can be transiently transfected into human cells, such as 293T/17. The surface expression can be detected with monoclonal antibodies (either IgG or ScFv) specific for the abovementioned extracellular domains 1, 2, 3, 4, 5, the linker between the domains, or other structure included in the anti-GD TCR CAR. Binding can be verified with specific secondary antibodies and quantified by flow cytometry. Additional target cell lines can be produced as needed by expression of human monoclonal antibodies on the surface of K562 cells.

Inflammatory and Autoimmune Diseases

The present invention also provides methods for preventing, treating and/or managing a disorder associated with GD T cells or cells expressing GD TCR (e.g., inflammatory and autoimmune diseases). The methods comprise administering to a subject in need thereof an anti-GD TCR CAR T cell of the invention that binds to the GD TCR expressing cell. In one aspect, the subject is a human. Non-limiting examples of inflammatory and autoimmune diseases associated with GD T cells include but are not limited to inflammatory, autoimmune disease and cancer. In some embodiments, the inflammatory and autoimmune disease is juvenile idiopathic arthritis, Behcet's disease, alopecia areata, systemic sclerosis, atherosclerosis, psoriasis, myositis, rheumatoid arthritis, inflammatory bowel disease, multiple sclerosis, type I diabetes, ankylosing spondylitis, autoimmune uveitis, Sjogren's syndrome, systemic lupus, and chronic cutaneous lupus.

In the methods of treatment, T cells isolated from a subject can be modified to express the appropriate anti-GD TCR CAR, expanded ex vivo and then reinfused into the subject. The modified T cells recognize target cells, such as GD T cells, and become activated, resulting in killing of the target cells.

Relapse may also occur in patients with an autoimmune disease. By infusing anti-GD TCR CART cells, the GD T cells are depleted to induce long-term remission, possibly due to the longevity of the anti-GD TCR CART cells.

To monitor anti-GD TCR CAR-expressing cells in vitro, in situ, or in vivo, anti-GD TCR CAR cells can further express a detectable marker. When the anti-GD TCR CAR binds the target, the detectable marker is activated and expressed, which can be detected by assays known in the art, such as flow cytometry. In one embodiment, the anti-GD TCR CAR includes a NFAT response element and a detectable marker, such as a green fluorescent protein (GFP), to detect and quantify anti-GD TCR CAR expressing cells.

Sources of T Cells

Prior to expansion and genetic modification, T cells are obtained from a subject. Examples of subjects include humans, dogs, cats, mice, rats, and transgenic species thereof. T cells can be obtained from a number of sources, including skin, peripheral blood mononuclear cells, bone marrow, lymph node tissue, cord blood, thymus tissue, tissue from a site of infection, ascites, pleural effusion, spleen tissue, and tumors. In certain embodiments of the present invention, any number of T cell lines available in the art, may be used. In certain embodiments of the present invention, T cells can be obtained from a unit of blood collected from a subject using any number of techniques known to the skilled artisan, such as Ficoll™ separation. In one preferred embodiment, cells from the circulating blood of an individual are obtained by apheresis. The apheresis product typically contains lymphocytes, including T cells, monocytes, granulocytes, B cells, other nucleated white blood cells, red blood cells, and platelets. In one embodiment, the cells collected by apheresis may be washed to remove the plasma fraction and to place the cells in an appropriate buffer or media for subsequent processing steps. In one embodiment of the invention, the cells are washed with phosphate buffered saline (PBS). In an alternative embodiment, the wash solution lacks calcium and may lack magnesium or may lack many if not all divalent cations. Again, surprisingly, initial activation steps in the absence of calcium lead to magnified activation. As those of ordinary skill in the art would readily appreciate a washing step may be accomplished by methods known to those in the art, such as by using a semi-automated "flow-through" centrifuge (for example, the Cobe 2991 cell processor, the Baxter Cyto-Mate, or the Haemonetics Cell Saver 5) according to the manufacturer's instructions. After washing, the cells may be resuspended in a variety of biocompatible buffers, such as, for example, Ca-free, Mg-free PBS, PlasmaLyte A, or other saline solution with or without buffer. Alternatively, the undesirable components of the apheresis sample may be removed and the cells directly resuspended in culture media.

In another embodiment, T cells are isolated from peripheral blood lymphocytes by lysing the red blood cells and depleting the monocytes, for example, by centrifugation through a PERCOLL™ gradient or by counterflow centrifugal elutriation. A specific subpopulation of T cells, such as $CD3^+$, $CD28^+$, $CD4^+$, $CD8^+$, $CD45RA^+$, and $CD45RO^+$ T cells, can be further isolated by positive or negative selection techniques. For example, in one embodiment, T cells are isolated by incubation with anti-CD3/anti-CD28 (i.e., 3×28)-conjugated beads, such as DYNABEADS® M-450 CD3/CD28 T, for a time period sufficient for positive selection of the desired T cells. In one embodiment, the time period is about 30 minutes. In a further embodiment, the time period ranges from 30 minutes to 36 hours or longer and all integer values there between. In a further embodiment, the time period is at least 1, 2, 3, 4, 5, or 6 hours. In yet another preferred embodiment, the time period is 10 to 24 hours. In one preferred embodiment, the incubation time period is 24 hours. For isolation of T cells from patients with leukemia, use of longer incubation times, such as 24 hours, can increase cell yield. Longer incubation times may be used to isolate T cells in any situation where there are few T cells as compared to other cell types, such in isolating tumor infiltrating lymphocytes (TIL) from tumor tissue or from immunocompromised individuals. Further, use of longer incubation times can increase the efficiency of capture of CD8+ T cells. Thus, by simply shortening or lengthening the time T cells are allowed to bind to the CD3/CD28 beads and/or by increasing or decreasing the ratio of beads to T cells (as described further herein), subpopulations of T cells can be preferentially selected for or against at culture initiation or at other time points during the process. Additionally, by increasing or decreasing the ratio of anti-CD3 and/or anti-CD28 antibodies on the beads or other surface, subpopulations of T cells can be preferentially selected for or against at culture initiation or at other desired time points. The skilled artisan would recognize that multiple rounds of selection can also be used in the context of this invention. In certain embodiments, it may be desirable to perform the selection procedure and use the "unselected" cells in the activation and expansion process. "Unselected" cells can also be subjected to further rounds of selection.

Enrichment of a T cell population by negative selection can be accomplished with a combination of antibodies directed to surface markers unique to the negatively selected cells. One method is cell sorting and/or selection via negative magnetic immunoadherence or flow cytometry that uses a cocktail of monoclonal antibodies directed to cell surface markers present on the cells negatively selected. For example, to enrich for CD4+ cells by negative selection, a monoclonal antibody cocktail typically includes antibodies to CD14, CD20, CD11b, CD16, HLA-DR, and CD8. In certain embodiments, it may be desirable to enrich for or positively select for regulatory T cells which typically express CD4+, CD25+, CD62L+, GITR+, and FoxP3+. Alternatively, in certain embodiments, T regulatory cells are depleted by anti-C25 conjugated beads or other similar method of selection. In other embodiments, subpopulation of T cells, such as, but not limited to, cells positive or expressing high levels of one or more surface markers e.g. CD28+, CD8+, CCR7+, CD27+, CD127+, CD45RA+, and/or CD45RO+ T cells, can be isolated by positive or negative selection techniques.

For isolation of a desired population of cells by positive or negative selection, the concentration of cells and surface (e.g., particles such as beads) can be varied. In certain embodiments, it may be desirable to significantly decrease the volume in which beads and cells are mixed together (i.e., increase the concentration of cells), to ensure maximum contact of cells and beads. For example, in one embodiment, a concentration of 2 billion cells/ml is used. In one embodiment, a concentration of 1 billion cells/ml is used. In a further embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells, or from samples where there are many tumor cells present (i.e., leukemic blood, tumor tissue, etc.). Such populations of cells may have therapeutic value and would be desirable to obtain. For example, using high concentration of cells allows more efficient selection of CD8+ T cells that normally have weaker CD28 expression.

In a related embodiment, it may be desirable to use lower concentrations of cells. By significantly diluting the mixture of T cells and surface (e.g., particles such as beads), interactions between the particles and cells is minimized. This selects for cells that express high amounts of desired antigens to be bound to the particles. For example, CD4+ T cells express higher levels of CD28 and are more efficiently captured than CD8+ T cells in dilute concentrations. In one embodiment, the concentration of cells used is $5\times10^6$/ml. In other embodiments, the concentration used can be from about $1\times10^5$/ml to $1\times10^6$/ml, and any integer value in between.

In other embodiments, the cells may be incubated on a rotator for varying lengths of time at varying speeds at either 2-10° C. or at room temperature.

T cells for stimulation can also be frozen after a washing step. Wishing not to be bound by theory, the freeze and subsequent thaw step provides a more uniform product by removing granulocytes and to some extent monocytes in the cell population. After the washing step that removes plasma and platelets, the cells may be suspended in a freezing solution. While many freezing solutions and parameters are known in the art and will be useful in this context, one method involves using PBS containing 20% DMSO and 8% human serum albumin, or culture media containing 10% Dextran 40 and 5% Dextrose, 20% Human Serum Albumin and 7.5% DMSO, or 31.25% Plasmalyte-A, 31.25% Dextrose, 5%, 0.45% NaCl, 10% Dextran 40 and 5% Dextrose, 20% Human Serum Albumin, and 7.5% DMSO or other suitable cell freezing media containing for example, Hespan and PlasmaLyte A, the cells then are frozen to −80° C. at a rate of 1° per minute and stored in the vapor phase of a liquid nitrogen storage tank. Other methods of controlled freezing may be used as well as uncontrolled freezing immediately at −20° C. or in liquid nitrogen.

In certain embodiments, cryopreserved cells are thawed and washed as described herein and allowed to rest for one hour at room temperature prior to activation using the methods of the present invention.

Also contemplated in the context of the invention is the collection of blood samples or apheresis product from a subject at a time period prior to when the expanded cells as described herein might be needed. As such, the source of the cells to be expanded can be collected at any time point necessary, and desired cells, such as T cells, isolated and frozen for later use in T cell therapy for any number of diseases or conditions that would benefit from T cell therapy, such as those described herein. In one embodiment a blood sample or an apheresis is taken from a generally healthy subject. In certain embodiments, a blood sample or an apheresis is taken from a generally healthy subject who is at risk of developing a disease, but who has not yet developed a disease, and the cells of interest are isolated and frozen for later use. In certain embodiments, the T cells may be expanded, frozen, and used at a later time. In certain embodiments, samples are collected from a patient shortly after diagnosis of a particular disease as described herein but prior to any treatments. In a further embodiment, the cells are isolated from a blood sample or an apheresis from a subject prior to any number of relevant treatment modalities, including but not limited to treatment with agents such as natalizumab, efalizumab, antiviral agents, chemotherapy, radiation, immunosuppressive agents, such as cyclosporin, azathioprine, methotrexate, mycophenolate, and FK506, antibodies, or other immunoablative agents such as CAMPATH, anti-CD3 antibodies, cytoxan, fludarabine, cyclosporin, FK506, rapamycin, mycophenolic acid, steroids, FR901228, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cells are isolated for a patient and frozen for later use in conjunction with (e.g., before, simultaneously or following) bone marrow or stem cell transplantation, T cell ablative therapy using either chemotherapy agents such as, fludarabine, external-beam radiation therapy (XRT), cyclophosphamide, or antibodies such as OKT3 or CAMPATH. In another embodiment, the cells are isolated prior to and can be frozen for later use for treatment following B-cell ablative therapy, e.g., Rituxan.

In a further embodiment of the present invention, T cells are obtained from a patient directly following treatment. In this regard, it has been observed that following certain cancer treatments, in particular treatments with drugs that damage the immune system, shortly after treatment during the period when patients would normally be recovering from the treatment, the quality of T cells obtained may be optimal or improved for their ability to expand ex vivo. Likewise, following ex vivo manipulation using the methods described herein, these cells may be in a preferred state for enhanced engraftment and in vivo expansion. Thus, it is contemplated within the context of the present invention to collect blood cells, including T cells, dendritic cells, or other cells of the hematopoietic lineage, during this recovery phase. Further, in certain embodiments, mobilization (for example, mobilization with GM-CSF) and conditioning regimens can be used to create a condition in a subject wherein repopulation, recirculation, regeneration, and/or expansion of particular cell types is favored, especially during a defined window of time following therapy. Illustrative cell types include T cells, B cells, dendritic cells, and other cells of the immune system.

In certain preferred embodiments, the Tcells to be transduced with an anti-GD TCR CAR are not themselves gamma delta T cells, due to the risk of having the CAR shield the epitope on the GD TCR in cis, thus making the gamma delta T cells resistant to anti-GD TCR CAR therapy, or the risk of having the GD TCR block the CAR in cis, thus making the CAR unable to bind a GD TCR in trans on another cell.

Activation and Expansion of T Cells

T cells are activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., *Transplant Proc.* 30(8):3975-3977, 1998; Haanen et al., *J. Exp. Med.* 190(9):13191328, 1999; Garland et al., *J. Immunol Meth.* 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, for example PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGF-β, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4$^+$) that is greater than the cytotoxic or suppressor T cell population ($T_C$, CD8$^+$). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

In one aspect, the invention includes a method for treating a GD T cell related disease in a subject. The method comprises: administering to the subject an effective amount of a genetically modified T cell comprising an isolated nucleic acid sequence encoding an anti-GD TCR CAR, wherein the isolated nucleic acid sequence comprises a nucleic acid sequence encoding an extracellular domain comprising an anti-GD TCR or fragment thereof, a nucleic acid sequence encoding a transmembrane domain, and a nucleic acid sequence encoding an intracellular signaling domain, thereby treating the GD T cell related disease in the subject.

In one embodiment, the GD T cell related disease is an inflammatory or autoimmune disease selected from the group consisting of juvenile idiopathic arthritis, Behcet's disease, alopecia areata, systemic sclerosis, atherosclerosis, psoriasis, myositis, rheumatoid arthritis, inflammatory bowel disease, multiple sclerosis, type I diabetes, ankylosing spondylitis, autoimmune uveitis, Sjogren's syndrome, systemic lupus, and chronic cutaneous lupus. In another embodiment, the GD T cell related disease is a GD T cell lymphoma (GDTCL) or a GD TCR-expressing T cell leukemia or lymphoma. In some embodiments, the GD TCR-expressing T cell leukemia or lymphoma also expresses alpha beta TCR.

Without wishing to be bound by any particular theory, the immune response elicited by the anti-GD TCR CAR-modified T cells may be an active or a passive immune response. In yet another embodiment, the modified T cell targets a GD T cell and/or a cell expressing a GD TCR.

In one embodiment, the fully-human anti-GD TCR CAR-genetically modified T cells of the invention may be a type of vaccine for ex vivo immunization and/or in vivo therapy in a mammal. In one embodiment, the mammal is a human.

With respect to ex vivo immunization, at least one of the following occurs in vitro prior to administering the cell into a mammal: i) expansion of the cells, ii) introducing a nucleic acid encoding an anti-GD TCR CAR to the cells or iii) cryopreservation of the cells.

Ex vivo procedures are well known in the art and are discussed more fully below. Briefly, cells are isolated from a mammal (e.g., a human) and genetically modified (i.e., transduced or transfected in vitro) with a vector expressing an anti-GD TCR CAR disclosed herein. The anti-GD TCR CAR-modified cell can be administered to a mammalian recipient to provide a therapeutic benefit. The mammalian recipient may be a human and the anti-GD TCR CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also includes compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the anti-GD TCR CAR-modified T cells of the invention are used in the treatment of GD-T-cell mediated diseases, disorders and conditions. In certain embodiments, the cells of the invention are used in the treatment of patients at risk for developing GD T cell related diseases. Thus, the present invention provides methods for the treatment or prevention of GD T cell related diseases comprising administering to a subject in need thereof, a therapeutically effective amount of the anti-GD TCR CAR-modified T cells of the invention.

The anti-GD TCR CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are in one aspect formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount," "an anti-body effective amount," or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, in some instances $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, activated T cells are administered to a subject. Subsequent to administration, blood is redrawn or apheresis is performed, and T cells are activated and expanded therefrom using the methods described here, and are then reinfused back into the patient. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol, may select out certain populations of T cells.

Administration of the cells of the invention may be carried out using any convenient means, including by aerosol inhalation, injection, ingestion, transfusion, implantation or transplantation. The compositions described herein may be administered to a patient transarterially, subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are administered by i.v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludarabine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin). (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAMPATH. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. The dose for CAMPATH, for example, will generally be in the range 1 to about 100 mg for an adult patient, usually administered daily for a period between 1 and 30 days. The preferred daily dose is 1 to 10 mg per day although in some instances larger doses of up to 40 mg per day may be used (described in U.S. Pat. No. 6,120,766).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

The Materials and Methods used in the performance of the experiments disclosed herein are now described.

Anti-GD TCR CAR Constructs and Sequences

All constructs were verified by Sanger sequencing and the plasmids were purified in larger scale with removal of endotoxins (Qiagen endofree Maxiprep).

The amino acid sequence for the anti-GD TCR CAR is the following (SEQ ID NO: 1):

```
MEFGLSWLFLVAILKGVQCGSDIQMTQTTSILSASLGDRVTITCRA

SCIDISNYLNWYQQNPDGTVKLLIYYTSRLHSGVPSRFSGSGSGTE

YSLTIKNLEQEDIATYFCQQGNMVPFTFGSGTKLEIKGGGGSGGGG

SGGGGSQVQLKESGPGLVAPSQSLSITCTVSGFSLTSYGVHWVRQP

PGKGLEWLGVIWASGTTDYNSALMSRLTISKDNSKSQVFLRMNSLQ

TDDTAMYYCARETTASFGYWGLGTLVTVSAASTTTPAPRPPTPAPT

IASQPLSLRPEACRPAAGGAVHTRGLDFACDSGIYIWAPLAGTCGV

LLLSLVITLYCKRGRKKLLYIFKQPFMRPVQTTQEEDGCSCRFPEE

EEGGCELRVKFSRSADAPAYQQGQNQLYNELNLGRREEYDVLDKRR

GRDPEMGGKPRRKNPQEGLYNELQKDKMAEAYSEIGMKGERRRGKG

HDGLYQGLSTATKDTYDALHMQALPPR
```

The regions of the polypeptide correspond to the following:

Italics: Signal peptide (human VH3-23): MEFGLSWLFLVAILKGVQC (SEQ ID NO: 2)

Bold: BamHI cloning site: GS

Underline: Light chain VL: DIQMTQTTSILSASL GDRVTITCRASQDISNYLNWYQQNPDGTVKLLIY YT SRL HSGVPSRFSGSGSGTEYSLTIKNLEQEDIATYFCQ QGNMVPFTFGSGTKLEIK (SEQ ID NO: 3) This is a deduced sequence of a mouse HP hybridoma (anti GD-TCR). The nucleotide sequence shown below is codon optimized.

```
                                    (SEQ ID NO: 4)
GS-linker: GGGGSGGGGSGGGGS
```

Double underline: Heavy chain VH: QVQLKESGPGL VAPSQSLSITCTVSGFSLTSYGVHWVRQPPGKGLEW-LGVIW ASGTTDYNSALMSRLTISKDNSKSQVFLRMN SLQ TDDTAMYYCARETTASFG YWGLGTLVTVSA (SEQ ID NO: 5) This is a deduced sequence of a mouse HP hybridoma (anti GD-TCR). The nucleotide sequence shown below is codon optimized.

Bold italic: Cloning site NheI: AS

Wavy underline: CD8 alpha hinge and transmembrane:

```
                                    (SEQ ID NO: 6)
TTTPAPRPPTPAPTIASQPLSLRPEACRPAAGGAVHTRGLDFACDSGIYI

WAPLAGTCGVLLLSLVITLYC
```

*Bold italics and*, wavy underlined, BspEI cloning site: SG

Bold and underlined: CD137:

```
                                    (SEQ ID NO: 7)
KRGRKKLLYIFKQPFMRPVQTTQEEDGCSCRFPEEEEGGCEL
```

Italics and Underlined: CD247(CD3zeta):

(SEQ ID NO: 8)
RVKFSRSADAPAYQQGQNQLYNELNLGRREEYDVLDKRRGRDPEMGGKPR

RKNPQEGLYNELQKDKMAEAYSEIGMKGERRRGKGHDGLYQGLSTATKDT

YDALHMQALPPR

The nucleic acid sequence for the anti-GD TCR CAR is the following (SEQ ID NO: 9):

ATGGAGTTTGGGCTGAGCTGGCTTTTTCTTGTGGCTATTTTAAAAG
GTGTCCAGTGCGGATCC<u>GATATCCAAATGACGCAAACTACGTCTAT
CCTGTCTGCCTCCTTGGGCGACCGGGTGACGATTACGTGCCGGGCA
TCTCAAGATATTAGTAACTATCTTAACTGGTATCAACAGAACCCTG
ACGGAACGGTGAAATTGCTCATTTACTACACTTCTAGACTTCATAG
TGGCGTGCCGTCCAGATTTTCCGGAAGTGGGTCAGGTACAGAATAC
TCACTGACTATTAAGAACCTGGAACAAGAGGACATAGCCACATATT
TTTGTCAGCAAGGTAATATGGTCCCTTTTACCTTCGGCAGTGGTAC
TAAGCTCGAAATAAA</u>GGGAGGAGGGGGTAGCGGAGGTGGCGGCTCA
GGCGGCGGCGGCAGT<u>CAGGTTCAACTTAAGGAATCCGGTCCCGGTC
TTGTAGCGCCAAGTCAGTCTCTCTATCACTTGTACGGTATCCGG
GTTCTCCCTTACGTCCTACGGGGTACACTGGGTTCGACAACCACCC
GGAAAGGGCCTGGAGTGGTTGGGCGTCATATGGGCAAGCGGAACTA
CGGATTATAACTCTGCCCTTATGTCTCGCCTCACCATTTCTAAAGA
TAATAGTAAAAGCCAGGTTTTTCTTCGCATGAACTCTCTCCAAACT
GATGACACAGCAATGTACTACTGCGCCAGGGAGACTACAGCGAGTT
TCGGTTATTGGGGCTTGGGCACACTGGTCACAGTTTCAGC</u>AGCTAG
CACCACGACGCCAGCGCCGCGACCACCAACACCGGCGCCCACCATC
GCGTCGCAGCCCCTGTCCCTGCGCCCAGAGGCGTGCCGGCCAGCGG
CGGGGGGCGCAGTGCACACGAGGGGGCTGGACTTCGCCTGTGATTC
CGGAATCTACATCTGGGCCCCTCTGGCCGGCACCTGTGGCGTGCTG
CTGCTGTCCCTGGTCATCACCCTGTACTGC**AAGCGGGGCAGAAAGA
AGCTGCTGTACATCTTCAAGCAGCCCTTCATGCGGCCTGTGCAGAC
CACACAGGAAGAGGACGGCTGTAGCTGTAGATTCCCCGAGGAAGAG
GAAGGCGGCTGCGAGCTG**AGAGTGAAGTTCAGCAGAAGCGCCGACG
CCCCTGCCTATCAGCAGGGCCAGAACCAGCTGTACAACGAGCTGAA
CCTGGGCAGACGGGAGGAATACGACGTGCTGGACAAGAGAAGAGGC
CGGGACCCTGAGATGGGCGGCAAGCCCAGACGGAAGAACCCCCAGG
AAGGCCTGTATAACGAACTGCAGAAAGACAAGATGGCCGAGGCCTA
CAGCGAGATCGGCATGAAGGGCGAGCGGAGAAGAGGCAAGGGCCAT
GACGGCCTGTACCAGGGCCTGAGCACCGCCACCAAGGACACCTACG
ACGCCCTGCACATGCAGGCCCTGCCTCCAAGATGA

Start (ATG) and stop (TGA) codons are shown in bold at the beginning and at the end of the nucleic acid sequence, respectively.

The regions of the nucleic acid correspond to the following:

Italics (with ATG start codon shown in bold): Human VH3-23 signal peptide:

(SEQ ID NO: 10)
ATGGAGTTTGGGCTGAGCTGGCTTTTTCTTGTGGCTATTTTAAAAGGTGT

CCAGTGC

Cloning site BamHI: GGATCC

Underline: Light chain variable region VL:

(SEQ ID NO: 11)
GATATCCAAATGACGCAAACTACGTCTATCCTGTCTGCCTCCTTGGGCGA

CCGGGTGACGATTACGTGCCGGGCATCTCAAGATATTAGTAACTATCTTA

ACTGGTATCAACAGAACCCTGACGGAACGGTGAAATTGCTCATTTACTAC

ACTTCTAGACTTCATAGTGGCGTGCCGTCCAGATTTTCCGGAAGTGGGTC

AGGTACAGAATACTCACTGACTATTAAGAACCTGGAACAAGAGGACATAG

CCACATATTTTTGTCAGCAAGGTAATATGGTCCCTTTTACCTTCGGCAGT

GGTACTAAGCTCGAAATAAA

GS-linker:

(SEQ ID NO: 12)
GGGAGGAGGGGGTAGCGGAGGTGGCGGCTCAGGCGGCGGCGGCAGT

Double underline: Heavy chain variable region VH:

(SEQ ID NO: 13)
CAGGTTCAACTTAAGGAATCCGGTCCCGGTCTTGTAGCGCCAAGTCAGTC

TCTCTCTATCACTTGTACGGTATCCGGGTTCTCCCTTACGTCCTACGGGG

TACACTGGGTTCGACAACCACCCGGAAAGGGCCTGGAGTGGTTGGGCGTC

ATATGGGCAAGCGGAACTACGGATTATAACTCTGCCCTTATGTCTCGCCT

CACCATTTCTAAAGATAATAGTAAAAGCCAGGTTTTTCTTCGCATGAACT

CTCTCCAAACTGATGACACAGCAATGTACTACTGCGCCAGGGAGACTACA

GCGAGTTTCGGTTATTGGGGCTTGGGCACACTGGTCACAGTTTCAGCA

Cloning site NheI: GCTAGC

Wavy underline: CD8 hinge and transmembrane:

(SEQ ID NO: 14)
ACCACGACGCCAGCGCCGCGACCACCAACACCGGCGCCCACCATCGCGTC

GCAGCCCCTGTCCCTGCGCCCAGAGGCGTGCCGGCCAGCGGCGGGGGGCG

CAGTGCACACGAGGGGGCTGGACTTCGCCTGTGATTCCGGAATCTACATC

TGGGCCCCTCTGGCCGGCACCTGTGGCGTGCTGCTGCTGTCCCTGGTCAT

CACCCTGTACTGC

Cloning site BspEI: TCCGGA (between CD8 hinge and transmembrance)

Bold and Underlined: CD137 signaling domain:

(SEQ ID NO: 15)
AAGCGGGGCAGAAAGAAGCTGCTGTACATCTTCAAGCAGCCCTTCATGCG

GCCTGTGCAGACCACACAGGAAGAGGACGGCTGTAGCTGTAGATTCCCCG

AGGAAGAGGAAGGCGGCTGCGAGCTG

Italics and Underlined: CD247 (CD3zeta) signaling domain:

(SEQ ID NO: 16)
AGAGTGAAGTTCAGCAGAAGCGCCGACGCCCCTGCCTATCAGCAGGGCCA

GAACCAGCTGTACAACGAGCTGAACCTGGGCAGACGGGAGGAATACGACG

TGCTGGACAAGAGAAGAGGCCGGGACCCTGAGATGGGCGGCAAGCCCAGA

CGGAAGAACCCCCAGGAAGGCCTGTATAACGAACTGCAGAAAGACAAGAT

GGCCGAGGCCTACAGCGAGATCGGCATGAAGGGCGAGCGGAGAAGAGGCA

AGGGCCATGACGGCCTGTACCAGGGCCTGAGCACCGCCACCAAGGACACC

TACGACGCCCTGCACATGCAGGCCCTGCCTCCAAGA.

Stimulation and Expansion of Primary Human T Cells

Primary human T cells were cultured in RPMI1640, 10% FBS and 10 mM HEPES, supplemented with 1% penicillin/streptomycin. T cells were isolated from voluntary healthy donors and provided by the human immunology core (University of Pennsylvania). Bulk T cells (CD4+ and CD8+) were stimulated with anti-CD3 and anti-CD28 beads (dynabeads, life technologies) at a bead:cell ratio of 3:1. 24 hours after stimulation, $10^6$ T cells were transduced with anti-GD TCR CAR constructs or a mock control (scFv-based chimeric antigen receptor against human CD19 or CD20) on day 1 after activation at a MOI of 5-10. In order to create T cells lacking surface TCRs and MHCI, CRISPR-mediated gene disruption of the TCR beta and beta-2 microglobulin locus was utilized. On day 3 after activation, RNAs encoding for Cas9 and guide RNAs targeting beta2 microglobulin and the TCR beta chain were delivered into the T cells by electroporation. For this purpose, T cell were washed and resuspended at a concentration of $10^8$ cells per milliliter in Optimem medium. T cells were mixed with Cas9 RNA (20 ug)/guide RNAs (10 ug) and electroporated with a BTX830 (Harvard Apparatus BTX) at 360V and for 1 ms. On day 4 after activation, RNA electroporation was repeated with just the guide RNAs under identical conditions as described above. CAR T cell expression was determined on day 10 after activation by flow cytometry; for this purpose, surface CAR expression was detected with biotinylated polyclonal donkey anti-mouse (Fab)-specific antibodies for 23 minutes at room temperature, washed twice and stained with streptavidin-PE for 23 minutes, followed by washing twice and flow-cytometric analysis of the cells (LSRII). CD3, MHCI negative T cells were quantified by staining the expanded T cells (10 days after activation) with anti-human CD3 and anti-human MHCI. CD3 negative T cells were isolated by negative selection using a magnetic sort (Miltenyi).

In Vitro Killing Assay

To assess the ability of anti-GD TCR CAR T cells to kill GD TCR positive target cells, a standard 4-hour chromium release assay was used. $5\times10^5$ target cells were loaded with 50 microCi of Na2 51CrO4 (Perkin Elmer) for 90 minutes, washed twice and resuspended in phenolred-free medium with 5% FBS. Anti-GD TCR or mock transduced T cells were coincubated with loaded target cells for 4 at various effector: target ratios and chromium release into the supernatant was measured with a microbeta 2 plate counter (Perkin Elmer).

In Vivo Efficacy Testing of Anti-GD TCR CAR T Cells

Anti-GD TCR CAR or control-CAR transduced T cells were expanded as described elsewhere herein. NSG mice with a humanized immune system (also known as BLT mice) were obtained from the University of Pennsylvania Stemcell and Xenograft core. Presence of GD T cells in these mice was verified by flow cytometric analysis 3 months after injection of human stem cells. For this purpose, EDTA-anticoagulated blood samples were obtained by retroorbital bleeding. GD T cells were identified as human $CD45^+$, $CD3^+$, $GD\ TCR^+$. In brief, 50 ul of EDTA-anticoagulated whole blood was stained with aforementioned anti-human antibodies for 23 minutes at room temperature, followed by red blood cell lysis and fixation of the cells (BD Facs lysing solution) for 10 minutes and flow cytometric analysis (LSRII, BD). CAR T cells or nontransduced T cells were created as mentioned above. Anti-GD TCR T CAR T cells or control CAR T cells (targeting either human CD19 or human CD20, or nontransduced) were expanded for 10 days, their CAR expression was determined by flow cytometry as described above and CD3 negative cells were magnetically isolated (Miltenyi). $1-2\times10^6$ were injected intravenously into BLT mice. GD TCR positive cell numbers in these mice were quantified 10 days after initial injection by flow cytometry with the above mentioned antibodies and gating strategy. All mouse experiments were conducted in accordance to an approved IACUC protocol.

To assess in vivo efficacy using a malignant GD T cell clone as a target, the T ALL line Loucy (ATCC CRL-2629) that is positive for GD TCR was used. Loucy cells were engineered to express clickbeetle green (CBG) luciferase co-expressing GFP and the GFP positive cells (BD Aria), which we refer to as Loucy-GFP, were sorted. 3×10e7 Loucy-GFP cells were injected on day 0 into a NOD-scid-gamma (NSG; NOD.Cg-Prkdcscid Il2rgtm1Wjl/SzJ) mice and the bioluminescence was determined on day 6, 14, 18, 24, 34, 46). After 14 days, anti-GD TCR CAR T cells (10e7 cells per mouse) were injected intravenously in a final volume of 150 µl. Bioluminescence was quantified with a Xenogen IVIS spectrum (Caliper Life Sciences). To do so, D-Luciferin potassium salt (Thermo Fisher) was injected intraperitoneally at a dose of 150 mg/kg body weight. Mice were anaesthetized with 2% isoflurane and luminescence was assessed 5 minutes after injection in automatic exposure mode. Total flux was quantified using Living Image 4.4 (PerkinElmer) by drawing rectangles of identical area around mice reaching from head to the 50% of the tail length; background bioluminescence was subtracted for each image individually. Cells for flow cytometry were obtained by retroorbital blood collection into EDTA tubes (BD). Whole blood was stained in BD trucount tubes with anti-human CD45 (clone HI30, APC-Cy7, Biolegend) for 20 minutes at room temperature according to the manufacturer's recommendations. Samples were analyzed on a LSRII, cell numbers were quantified by gating on GFP/CD45 positive cells.

Competitive Binding of Different Anti GD-TCR Clones

In order to determine if the anti GD-TCR antibody clone (referred to as HP, also known as 5A6.E9 (ThermoFisher) or anti-TCR δ1; this is a pan GD-TCR antibody) used to make the CAR binds to the same epitope as other anti-GD TCR clones (namely IMMU510, Beckman Coulter, and 11F2, BD), flow cytometry-based competition assays were performed. Primary human GD T cells were preincubated with 1, 2, 5, or 10 ul of either HP-PE (ThermoFisher) or IMMU510 FITC (Beckman Coulter) for 25 minutes at 4° C. in PBS-2% FBS-2 mM EDTA, washed the cells twice and then stained the HP pre-stained cells with IMMU510 and the IMMU510 pre-stained cells with HP. Antibody binding was analyzed on an LSRII (BD) and binding blockade by preincubation was quantified by comparing the mean fluorescence intensity (MFI) of HP and IMMU510 with and without pre-staining with IMMU510 and HP, respectively. In order to determine if HP and 11F2 bind to the same epitope, HP was purified from tissue culture supernatant of 5A6.E9 hybridoma cells (HB-9772) with protein G agarose (ThermoFisher) according to the manufacturer's recommendations. HP was labeled with AF647 with and AF647 antibody labeling kit (ThermoFisher) according to the manufacturer's recommendations. Primary human T cells (expanded with anti CD3 and anti CD28 beads as described above, which yields a lower percentage of GD T cells) were stained either with HP-AF647 or 11F2-PE (BD) or co-stained with both antibodies at the same time for 25 minutes at 4C. Binding was analyzed on an LSRII and binding of HP and 11F2 only was compared to staining in presence of 11F2 and HP, respectively.

The results of the experiments are now described.

Example 1

Human T cells were engineered to express an scFv-based CAR against the GD TCR. Anti-GD TCR CARs were effectively expressed on primary human T cells, and exposure of GD T cells to anti-GD TCR CART cells eliminated or significantly reduced GD T cells both in vitro and in humanized immune system mice in vivo.

As shown in FIG. 1, cutaneous GD T cell lymphomas have a poor prognosis. The Kaplan and Meier plots of patients with cutaneous T-cell lymphoma depict the survival of individuals with cutaneous T-cell lymphoma according to T-cell-receptor immunophenotype. A comparison was made between patients with alpha-beta (dotted line) and gamma-delta (solid line) cutaneous T-cell lymphomas (Toro et al., Blood 2003; 101:3407-3412).

Figure 2:
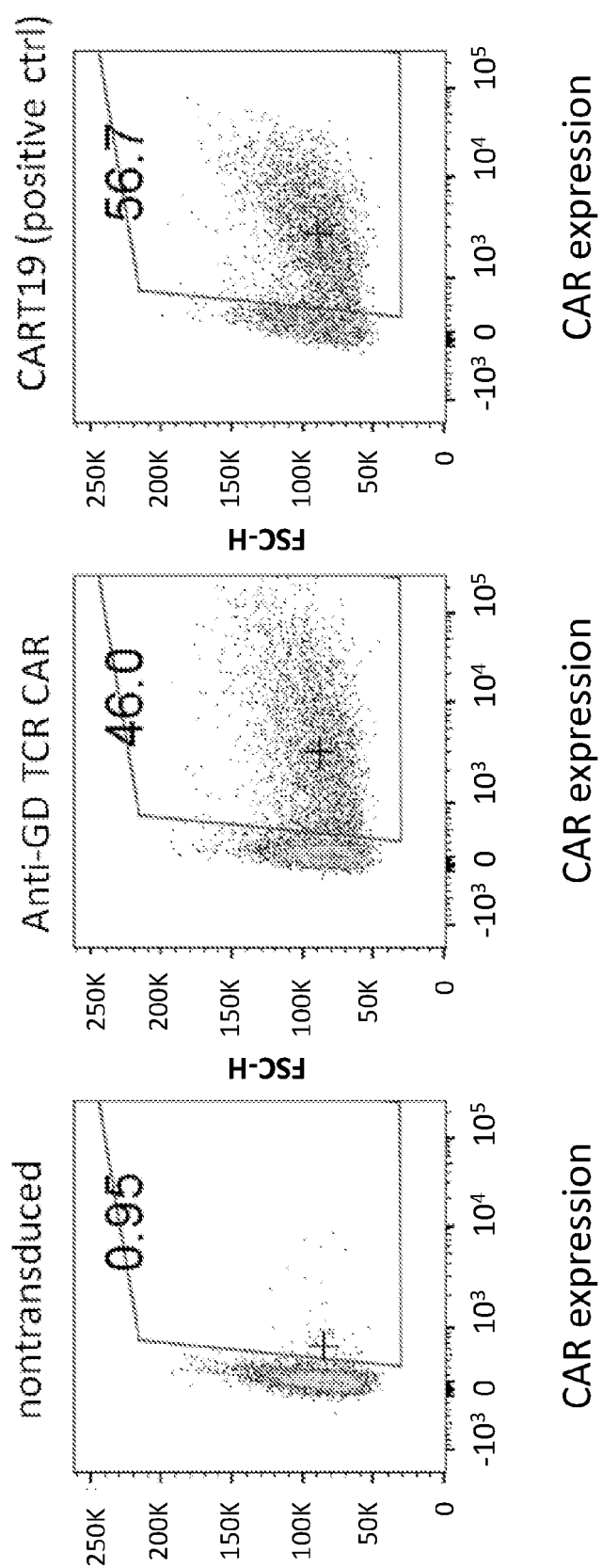
FIG. 2 is a panel of flow cytometry plots demonstrating that anti-GD T cell receptor CAR (anti-GD TCR CAR) can be expressed on primary human T cells. Primary human T cells were activated with anti-CD3/CD28 beads for 24 hours before they were transduced with lentiviral particles encoding the anti-GD TCR CAR and CART19 as positive control. 10 days after activation, the cells were stained with polyclonal anti-mouse IgG-biotin which was detected with streptavidin-BV421.

FIG. 2 demonstrates that anti-GD TCR CAR can be expressed on primary human T cells. Primary human T cells were activated with anti-CD3/CD28 beads for 24 hours before they were transduced with lentiviral particles coding for the anti-GD TCR CAR and CART 19 as positive control. 10 days after activation, the cells were stained with polyclonal anti-mouse IgG-biotin which was detected with streptavidin-BV421. The anti-GD TCR CAR used in this experiment was expressed under an EF1a promoter, and consisted of a CD8a signal peptide, a scFv, a CD8a hinge and transmembrane, CD137 and CD247 signaling domains.

Figure 3:
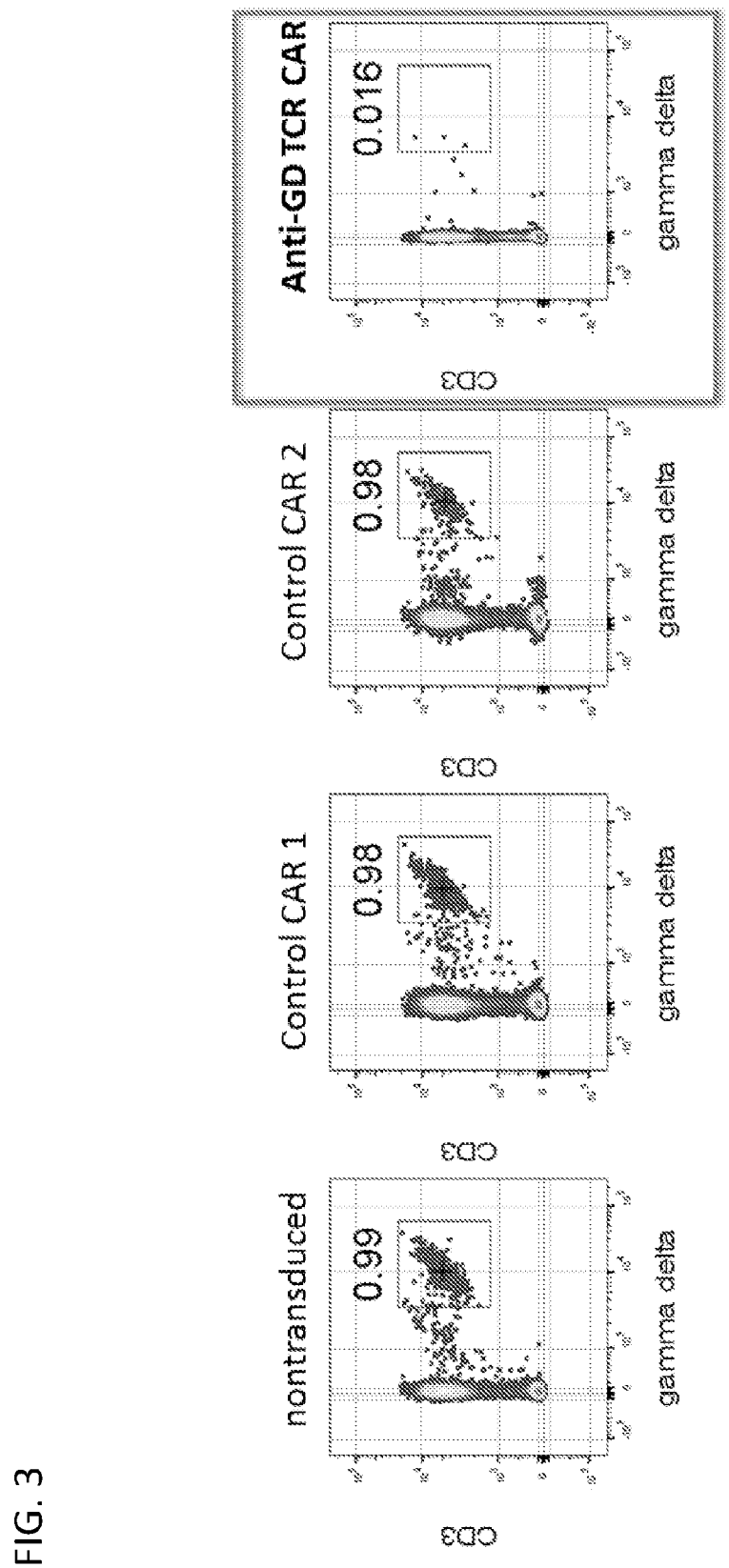
FIG. 3 is a panel of flow cytometry plots showing that anti-GD TCR CAR T cells eliminate primary human GD T cells in vitro. Primary human T cells were activated and transduced with control CARs or anti-GD TCR CAR and expanded for 10 days, after which the presence of GD T cells was determined by flow cytometry. GD T cells are absent from the anti-GD TCR CAR culture and there is no expansion of GD T cells due to targeting of their TCR (these data also indicate that binding of the anti-GD CAR to the GD TCR does not proliferate GD Tcells beyond the capacity of the anti-GD CARTs to eliminate them).

FIG. 3 illustrates that anti-GD TCR CAR T cells eliminate GD T cells in vitro. Primary human T cells were activated and transduced with control CARs or anti-GD TCR CAR and expanded for 10 days, after which the presence of GD T cells was determined by flow cytometry. GD T cells are absent from the anti-GD TCR CAR culture and there is no expansion of GD T cells due to targeting of their TCR (these data also indicate that binding of the anti-GD CAR to the GD TCR does not proliferate GD T cells beyond the capacity of the anti-GD CARTs to eliminate them).

Figure 4:
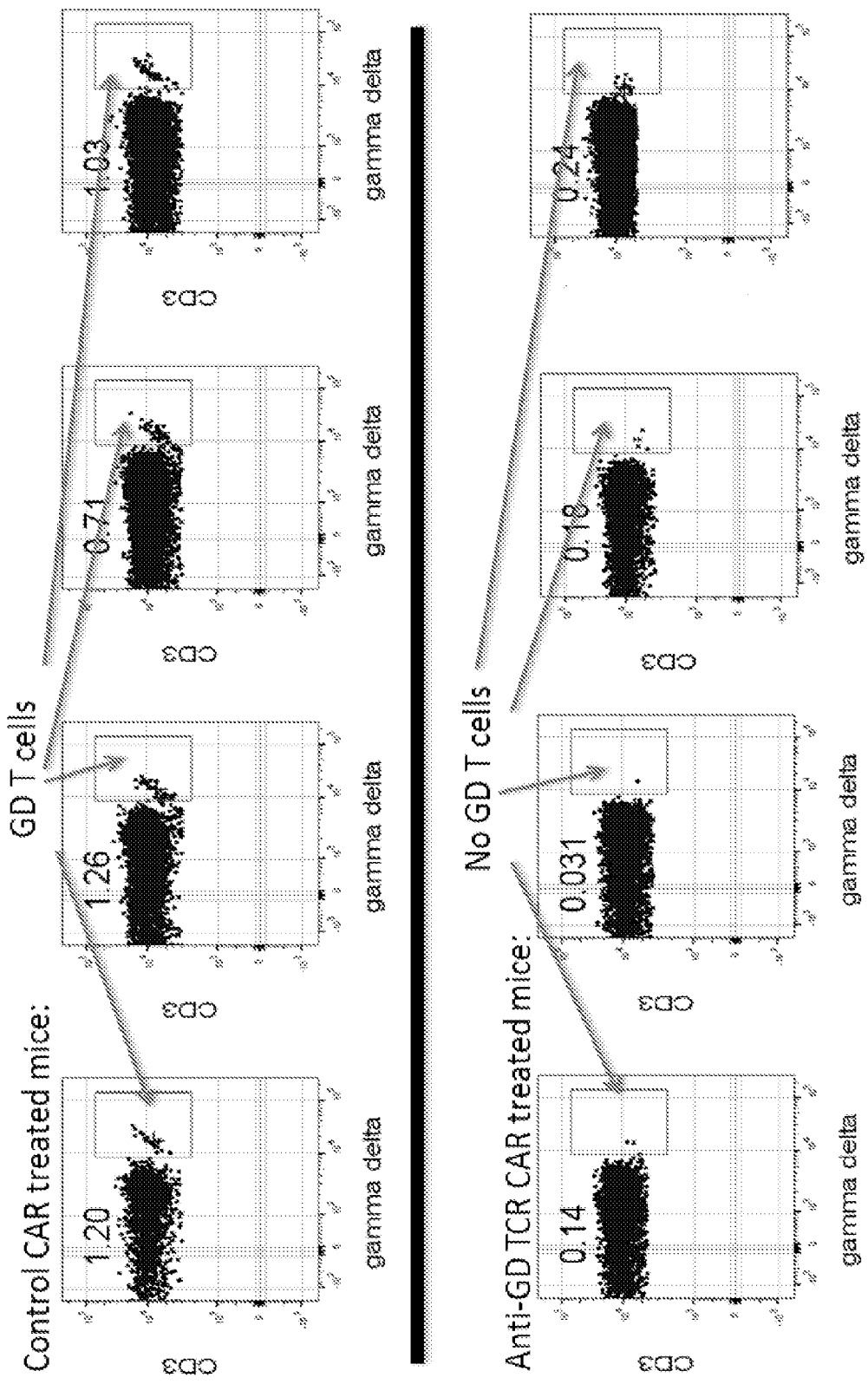
FIG. 4 is a panel of flow cytometry plots showing that anti-GD TCR CAR T cells eliminate primary human GD T cells in vivo. NSG mice were implanted with human thymus and CD34 positive bone marrow cells (i.e. stem cells). A humanized immune system was allowed to develop for 3 months. After verification of engraftment of human immune cells by flow cytometry, mice were treated with control or anti-GD TCR CAR T cells. The CAR T cells were engineered to not express CD3 and MHCI by CRISPR/CAS mediated gene disruption which was performed by RNA electroporation during T cell expansion. 9 days after T cell injection (2.5e6 cells i.v. per mouse), the presence of GD T cells was determined by flow cytometry. Flow cytometry plots above show CD3/GD TCR positive cells in the control CAR treated mice, whereas GD T cells are absent in the anti-GD TCR CAR treated mice. Cells were pre-gated for single cells→SSC low/human CD45 positive cells.

FIG. 4 illustrates that anti-GD TCR CAR T cells eliminate GD T cells in vivo. NSG mice were implanted with human thymus and CD34 positive bone marrow cells (i.e. stem cells). A humanized immune system was allowed to develop for 3 months. After verification of engraftment of human immune cells by flow cytometry, mice were treated with control or anti-GD TCR CAR T cells. The CAR T cells were engineered to not express CD3 and MHCI by CRISPR/CAS mediated gene disruption which was performed by RNA electroporation during T cell expansion. 9 days after T cell injection (2.5e6 cells i.v. per mouse), the presence of GD T cells was determined by flow cytometry. CD3/GD TCR cells were present in the control CAR treated mice and absent in the anti-GD TCR CAR treated mice.

Example 2

Figure 5:
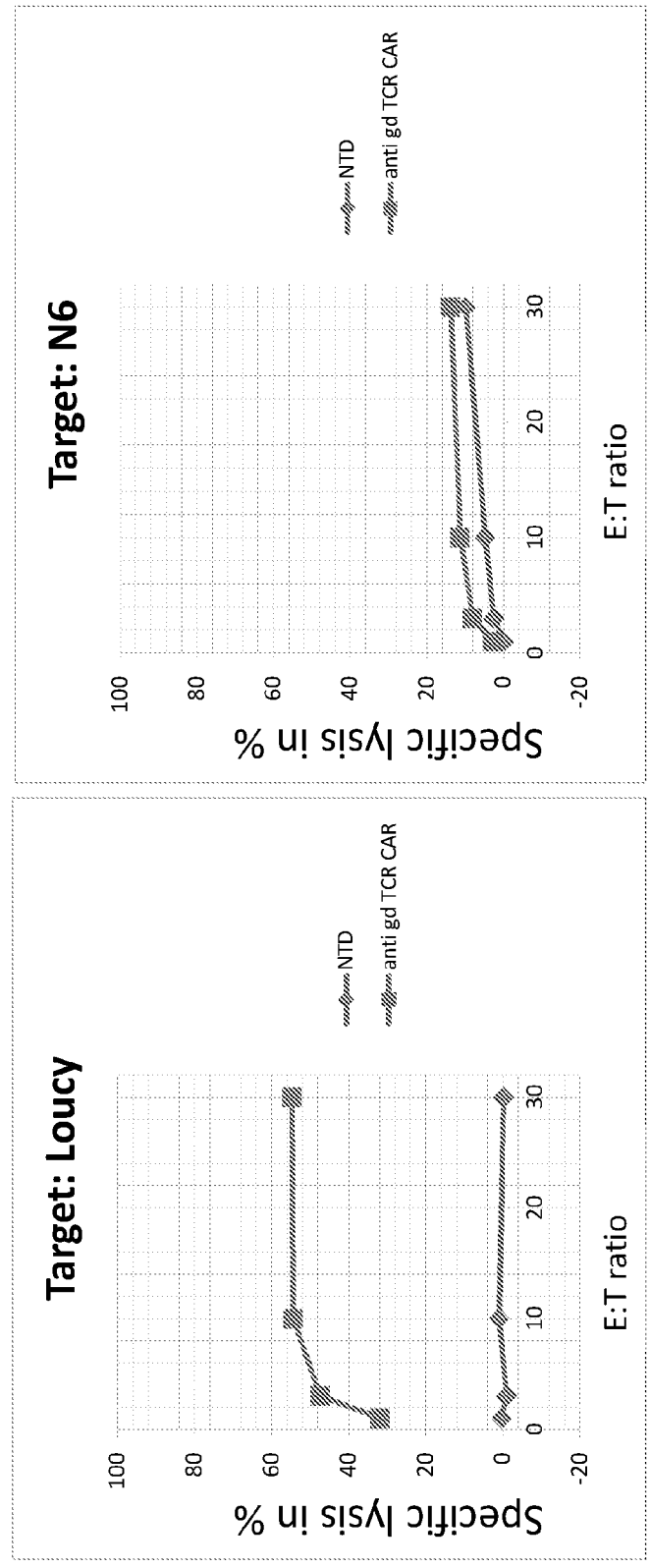
FIG. 5 is a panel of graphs that show the results of a 4 hour chromium release assay. Target cells (Loucy T-ALL (GD TCR positive) or N6 B cells (GD TCR negative) were mixed with either non-transduced or anti-GD TCR T cells at indicated effector to target (E:T) ratios. Anti-GD TCR CAR T cells specifically killed Loucy T-ALL cells which are GD TCR positive as opposed to N6 (Nalm6) cells (GD TCR negative).

Target cells (Loucy T-ALL (GD TCR positive) or N6 B cells (GD TCR negative) were mixed with either non-transduced or anti-GD TCR T cells at indicated effector to target (E:T) ratios. Anti-GD TCR CAR T cells specifically killed Loucy T-ALL cells which are GD TCR positive as opposed to N6 (Nalm6) cells (GD TCR negative). The results are shown in FIG. 5, which is a panel of graphs that show the results of a 4 hour chromium release assay.

Figure 6A:
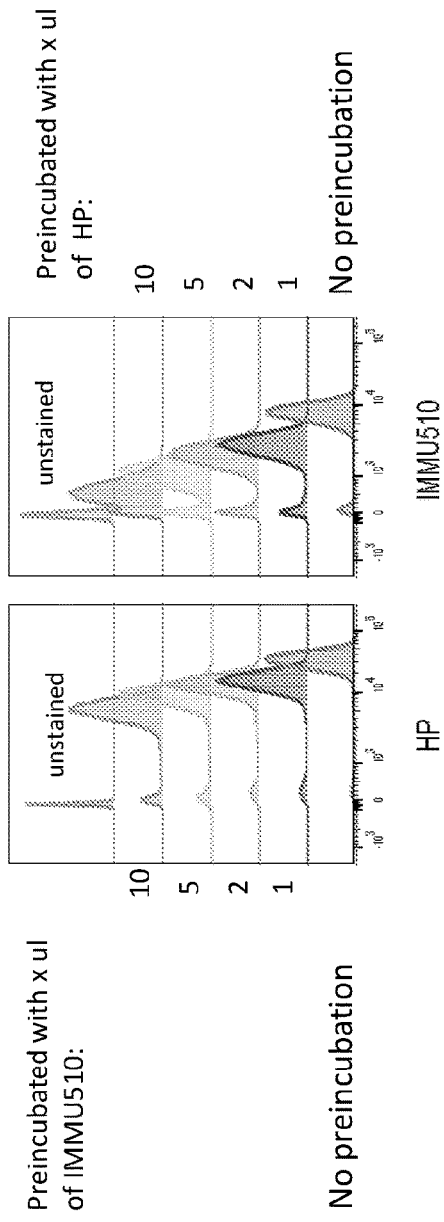
FIGS. 6A and 6B illustrate that the anti-GD TCR clone (called HP or 5A6.E9) used in the anti-GD TCR CAR and the separate IMMU510 anti-GD TCR clone bind to the same/overlapping epitope on the GD TCR. Human primary GD T cells were preincubated with different amounts (1, 2, 5, 10 ul) of one clone and then were stained with the other clone.
Figure 6B:
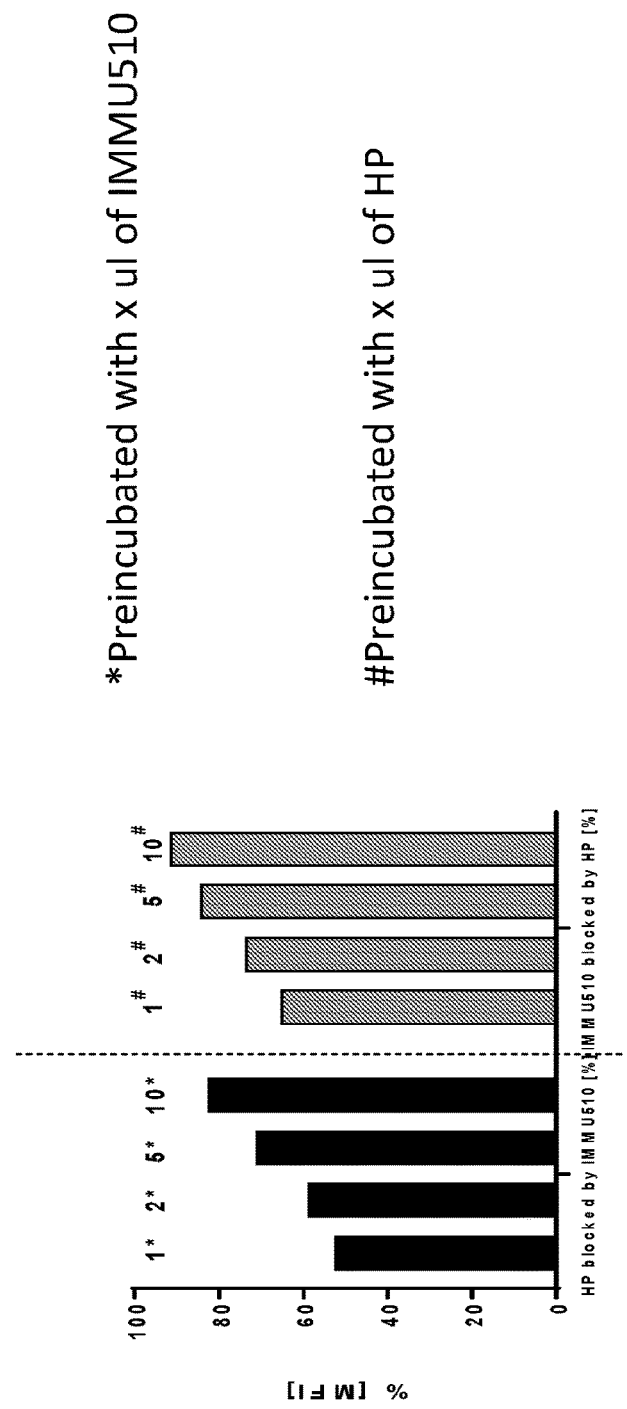

FIGS. 6A and 6B illustrate that the HP anti-GD TCR clone used in the anti-GD TCR CAR and a separate IMMU510 anti-GD TCR clone bind to the same/overlapping epitope on the GD TCR. Human primary GD T cells were preincubated with different amounts (1, 2, 5, 10 ul) of one clone and then were stained with the other clone. FIG. 6A illustrates a panel of histograms that show binding of HP (left) and IMMU510 (right) after preincubation with various amounts of the other clone (IMMU510 left, or HP right, respectively). Preincubation with one of the clones resulted in reduced binding of the other clone. FIG. 6B illustrates a bar graph where MFI after preincubation (setup as in FIG. 6A) was compared to staining without preincubation and is expressed as blocking percentage. Preincubation with IMMU510 blocked binding of HP (left) and preincubation with HP blocked binding of IMMU510 (right).

Figure 7:
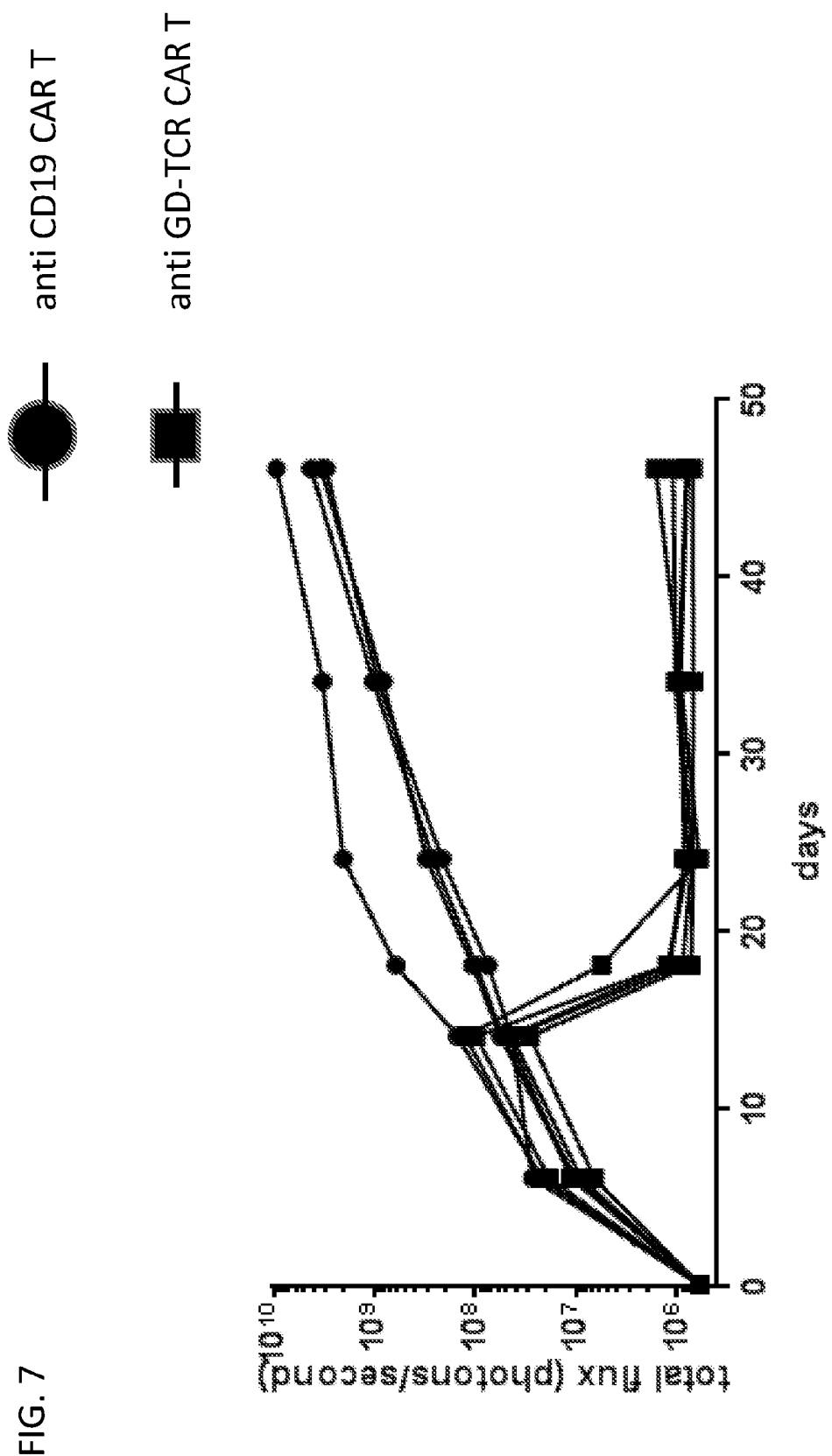
FIG. 7 illustrates that anti-GD TCR CAR T cells eliminated Loucy-ALL cells (GD TCR positive) in vivo. Loucy T-ALL cells (GD TCR positive) were injected into NSG mice on day 0 ($3\times10^7$ cells per mouse). Mice were injected with anti-CD19 CAR T cells (circle) or anti-GD-TCR CAR T cells (square) on day 14 ($1\times10^7$ cells per mouse). Day 0 represents imaging of mice prior to injection (n=2). X axis displays time in days. Y axis displays bioluminescence in photons/second. The anti-GD TCR CAR T cells eliminated Loucy cells. The remission lasted until the end of the experiment on day 46 (p=0.016). Each line on the graph represents one mouse.

FIG. 7 illustrates that anti-GD TCR CAR T cells eliminated Loucy-ALL cells (GD TCR positive) in vivo. Loucy T-ALL cells (GD TCR positive) were injected into mice on day 0 ($3\times10^7$ cells per mouse). Mice were injected with CD19 CAR (black) or anti-GD-TCR CAR T cells (red) on day 14 ($1\times10^7$ cells per mouse). Day 0 represents imaging of mice prior to injection (n=2). X axis displays time in days. Y axis displays bioluminescence in photons/second. The anti-GD TCR CAR T cells eliminated Loucy cells. The remission lasted until the end of the experiment on day 46 (p=0.016).

Figure 8A:
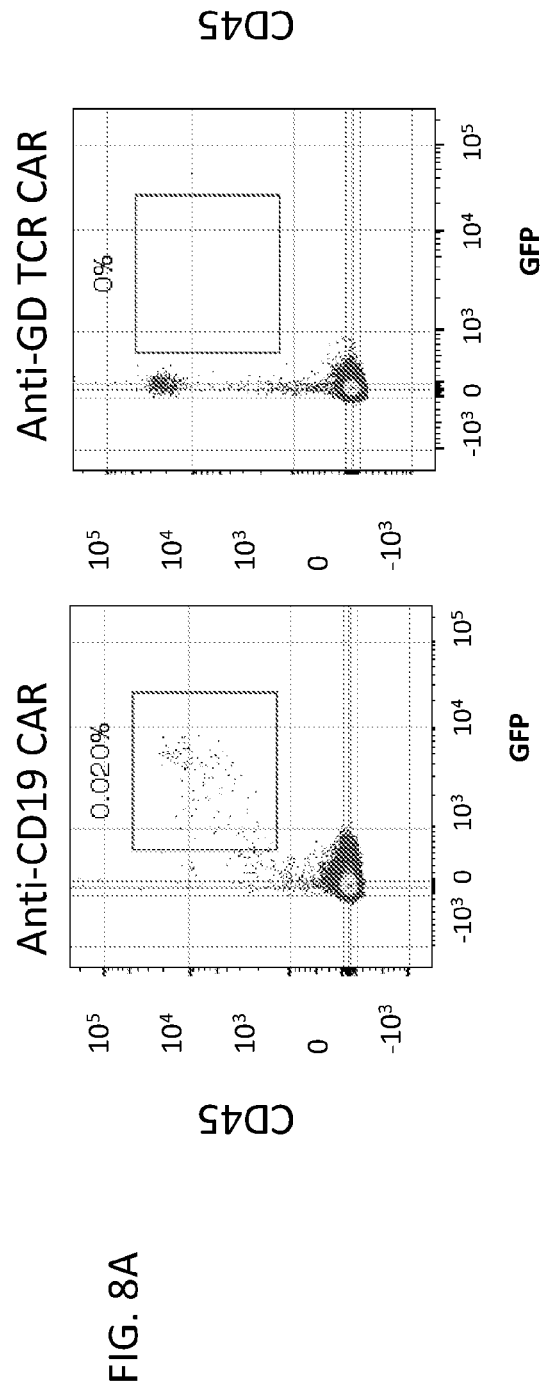
FIGS. 8A and 8B illustrate flow cytometry results showing that anti-GD TCR CAR T cells eliminate Loucy GD T cells in vivo. Blood samples were obtained 47 days after injection of Loucy T cells into NSG mice. Loucy T cells are detected by GFP expression, which is expressed together with click beetle luciferase, and staining with CD45.
Figure 8B:
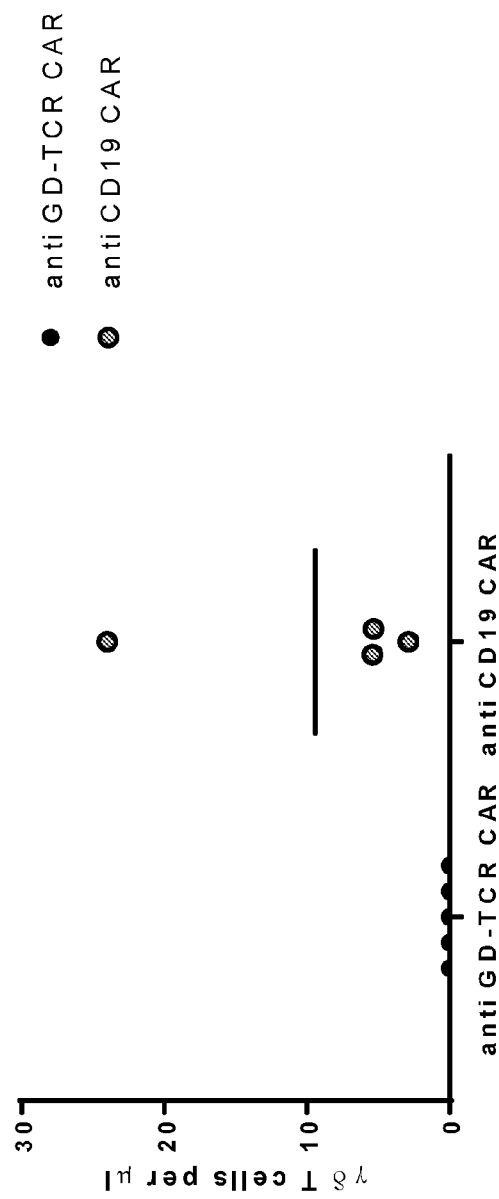

FIGS. 8A and 8B illustrate flow cytometry results showing that anti-GD TCR CAR T cells eliminate Loucy GD T cells in vivo. Blood samples were obtained 47 days after injection of Loucy T cells into NSG mice. Loucy T cells are detected by GFP expression, which is expressed together with click beetle luciferase, and staining with CD45. FIG. 8A is a panel of flow cytometry plots showing that anti-CD19 CAR treated mice developed leukemia with Loucy T cells being detectable in the peripheral circulation (left), while anti-GD TCR CAR treated mice did not demonstrate detectable Loucy GD T cells. FIG. 8B is a plot showing the quantification of GD T cells in the peripheral circulation (day 47, blood), demonstrating eradication of Loucy GD T cells by anti-GD CAR T cells (p=0.0072).

FIGS. 9A-9C illustrate that the anti-GD TCR clone (called HP or 5A6.E9) used in the anti-GD TCR CAR, and another anti-GD TCR clone (called F2) bind to the same or overlapping epitope on the GD TCR. Primary human T cells (after expansion with anti CD3 and anti CD28 beads, therefore, the percentage of GD T cells is lower than prior to activation) were stained with 5A6.E9-AF647 or 11F2-PE. Staining was compared to fluorescence minus one (FMO) samples that were unstained. FSC-H represents the size of the cells. FIG. 9A shows that the percentage of 5A6.E9 stained cells did not change when co-stained with 11F2 (0.42 vs 0.43%). FIG. 9B shows that the binding of 11F2 was almost completely abolished by co-incubation with 5A6.E9, indicating that the 2 clones bind to the same or overlapping epitopes. FIG. 9C shows that when displaying both the PE and the AF647 channel, staining with 11F2 resulted in a discrete PE positive population (left panel), while co-incubation of the cells with both 11F2 and 5A6.E9 resulted in disappearance of the PE positive population (right panel).

The present invention relates to the discovery that chimeric receptors can be used to target GDTCR to treat various GD T cell conditions and/or diseases. The anti-GD TCR CAR approach disclosed herein can be very powerful as GDTCLs include many favorable characteristics for CAR therapy: (I) The GD T cell population is uniquely identified by the expression of a GD T cell receptor (GD TCR) that is not expressed on any other human cell type; thus, on-target/off-tissue toxicity is not expected. (II) CAR therapy has been more efficacious in treating hematopoietic malignancies (such as GDTCL) as compared to solid tumors, thus the feasibility of the target is favorable. (III) The long-term loss of GD T cells will not result in widespread immunosuppression (compared to targeting CD19, CD20, CD38, CD2, CD3, CD4, CD5, CD8 or CD37), as GD T cells comprise approximately 5% of the peripheral T cells, and GD T cell-deficient mice have no significant clinical phenotypic defects at baseline.

Therefore this invention includes a novel therapeutic approach that targets the GD TCR with CAR engineered T cells, potentially resulting in long-term remission of a highly lethal and previously incurable cancer. Beyond the potentially curative aspect of this approach, the present invention allows invaluable insight into GD T cell biology, since eradication of GD T cells will uncover their specific functions in humans, which to date are mostly speculative. In addition to being a novel and potentially curative therapy for GDTCLs, this invention could lead to lasting remissions for the autoimmune diseases mentioned previously herein, which could provide a targeted effective therapy that minimizes the side effects associated with generalized immunosuppression.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. An isolated nucleic acid comprising a nucleic acid sequence encoding an anti-GD TCR CAR comprising the amino acid sequence of SEQ ID NO: 1.

2. The isolated nucleic acid of claim 1, wherein the nucleic acid sequence encoding the anti-GD TCR CAR comprises SEQ ID NO: 9.

3. The isolated nucleic acid of claim 1, wherein the light chain is encoded by the nucleic acid sequence of SEQ ID NO: 11 or the heavy chain is encoded by the nucleic acid sequence of SEQ ID NO: 13.

4. The isolated nucleic acid of claim 1, wherein the VH3-23 signal peptide is encoded by the nucleic acid sequence of SEQ ID NO: 10.

5. The isolated nucleic acid of claim 1, wherein the CD8 alpha chain hinge and transmembrane domain are encoded by a nucleic acid sequence comprising the sequence of SEQ ID NO: 14.

6. The isolated nucleic acid of claim 1, wherein the nucleic acid sequence encoding the peptide linker comprises SEQ ID NO: 12.

7. The isolated nucleic acid of claim 1, wherein the nucleic acid sequence encoding the CD137 intracellular domain comprises SEQ ID NO: 15.

8. The isolated nucleic acid of claim 1, wherein the nucleic acid sequence encoding the CD3 zeta signaling domain comprises SEQ ID NO: 16.

9. A vector comprising the isolated nucleic acid of claim 1.

10. The vector of claim 9, wherein the vector is a lentiviral vector.

11. The vector of claim 10, wherein the vector is a RNA vector.

12. An isolated anti-GD TCR CAR encoded by the nucleic acid of claim 1.

13. A genetically modified cell comprising the isolated nucleic acid of claim 1.

14. The cell of claim 13, wherein the cell expresses the anti-GD TCR CAR and has high affinity for GD T cells.

15. The cell of claim 13, wherein the cell expresses the anti-GD TCR CAR and induces killing of GD T cells or cells expressing GD TCR.

16. The cell of claim 13, wherein the cell is selected from the group consisting of a helper T cell, a cytotoxic T cell, a memory T cell, regulatory T cell, a natural killer cell, a cytokine induced killer cell, a cell line thereof, a T memory stem cell and other effector cell.

17. The cell of claim 13, wherein an endogenous CD3 and an endogenous MHCI of the cell has been knocked out using a CRISPR/CAS system.

18. A method for treating a GD T cell related disease in a subject, the method comprising: administering to the subject an effective amount of the genetically modified T cell of claim 13.

19. The method of claim 18, wherein the GD T cell related disease is an inflammatory or autoimmune selected from the group consisting of juvenile idiopathic arthritis, Behcet's disease, alopecia areata, systemic sclerosis, atherosclerosis, psoriasis, myositis, rheumatoid arthritis, inflammatory bowel disease, multiple sclerosis, type I diabetes, ankylosing spondylitis, autoimmune uveitis, Sjogren's syndrome, systemic lupus, and chronic cutaneous lupus.

20. The method of claim 18, wherein the GD T cell related disease is a GD T cell lymphoma (GDTCL).

21. The method of claim 18, wherein the subject is a human.

22. The method of claim 18, wherein the modified T cell targets a GD T cell or a cell expressing GD TCR.

* * * * *